(12) United States Patent
Ueno et al.

(10) Patent No.: US 6,451,988 B1
(45) Date of Patent: Sep. 17, 2002

(54) NAPHTHOL DERIVATIVES

(75) Inventors: Ryuzo Ueno, Nishinomiya (JP);
Masaya Kitayama, Takarazuka (JP);
Kenji Minami, Sennan (JP); Hiroyuki Wakamori, Hikami-gun (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 10/031,115

(22) PCT Filed: May 15, 2001

(86) PCT No.: PCT/JP01/04006
§ 371 (c)(1),
(2), (4) Date: Jan. 16, 2002

(87) PCT Pub. No.: WO01/87859
PCT Pub. Date: Nov. 22, 2001

(51) Int. Cl.⁷ .................... C07D 263/57; C07D 413/02; C07D 417/02; C09B 29/15; C09B 35/378
(52) U.S. Cl. ................ 534/655; 534/796; 534/797; 534/799; 548/106; 548/156; 548/159; 548/180; 548/218; 548/220; 548/224; 548/305.4
(58) Field of Search ................ 534/655, 796, 534/797, 799; 548/106, 156, 180, 220, 224, 305.4

(56) References Cited

FOREIGN PATENT DOCUMENTS

| EP | 765858 A1 | 4/1997 |
| EP | 872477 A1 | 10/1998 |
| EP | 1043364 A1 | 10/1999 |

OTHER PUBLICATIONS

International Search Report.

*Primary Examiner*—Fiona T. Powers
(74) *Attorney, Agent, or Firm*—Sughrue Mion, PLLC

(57) ABSTRACT

Novel naphthol derivatives, and various azo compounds and metal complexes prepared by using the derivatives are provided.

The instant invention provides naphthol derivatives represented by general formula (1);

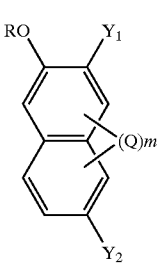

(1)

wherein at least one of $Y_1$ and $Y_2$ is a group represented by formula (2);

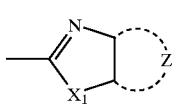

(2)

wherein $X_1$ is —O—, —S— or —NH—; and Z is an optionally substituted aromatic group or heterocyclic group having conjugated double bonds,
and salts thereof; mono-, bis-, and trisazo compounds prepared from the derivatives; and metal complexes containing the derivatives as the ligand.

7 Claims, 7 Drawing Sheets

NAPHTHOL DERIVATIVES

TECHNICAL FIELD

The present invention relates to a novel naphthol derivative, which can be used as a coupler component of an azo compound, which is useful for dyes, pigments, photosensitive materials and the like. The present invention also relates to an azo compound and a metal complex which are synthesized with the naphthol derivative.

BACKGROUND OF THE INVENTION

Naphthol derivatives are the most economical compounds among the condensed aromatic compounds, which can form conjugated polyene systems and have adsorption in the electron band, and are easily used as raw materials for synthesis of chemical materials. Therefore, it has hitherto been used for preparing various compounds, particularly for dyes, pigments, photosensitive materials and the like.

Some naphthol derivatives are known including 3- or 6-substituted 2-hydroxynaphthalene such as 2hydroxy-3phenylaminocarbonyl naphthalene and 2hydroxy-6-phenylaminocarbonyl naphthalene and those having further substituents, such as alkyl and alkoxy groups, on the phenyl group.

However, only 2-hydroxy-3,6-dihydroxycarbonyl naphthalene and derivatives thereof having amide or ester bonding, which are disclosed in WO98/16513, have been known as the naphthalene derivatives having substituents at both of 3- and 6-positions of 2-hydroxynaphthalene.

SUMMARY OF THE INVENTION

An object of the present invention is to provide a novel naphthol derivative, which is useful as a raw material for synthesizing chemical materials. Another object of the present invention is to provide monoazo, bisazo and trisazo compounds as well as metal complexes prepared with the novel naphthol derivative of the present invention.

Accordingly, the present invention provides a naphthol derivative represented by general formula (1):

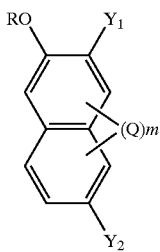

(1)

wherein each $Y_1$ and $Y_2$ is independently selected from the group consisting of carboxyl, esterified carboxyl, amidated carboxyl and a group represented by general formula (2)

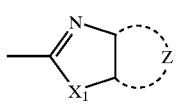

(2)

wherein
$X_1$ is —O—, —S— or —NH—,
Z is an optionally substituted aromatic or heterocyclic group having conjugated double bonds, provided that at least one of $Y_1$ and $Y_2$ is a group represented by formula (2);

Q is selected from the group consisting of optionally branched alkyl and alkoxy groups each having 1–6 carbon atoms, halogen atom, nitro and nitroso groups, m is an integer of 0–3;

R is selected from the group consisting of hydrogen atom, alkaline metal, optionally branched and optionally substituted alkyl and acyl groups each having 1–20 carbon atoms and phenyl alkyl group;

and a salt thereof.

In another embodiment of the present invention, novel monoazo, bisazo and trisazo compounds, which may be prepared with the naphthol derivative or the salt thereof of the present invention are also provided.

In a further embodiment of the present invention, a novel metal complex, which may be prepared with the naphthol derivative or the salt thereof of the present invention is also provided.

DETAILED DESCRIPTION OF THE INVENTION

Figure 1:
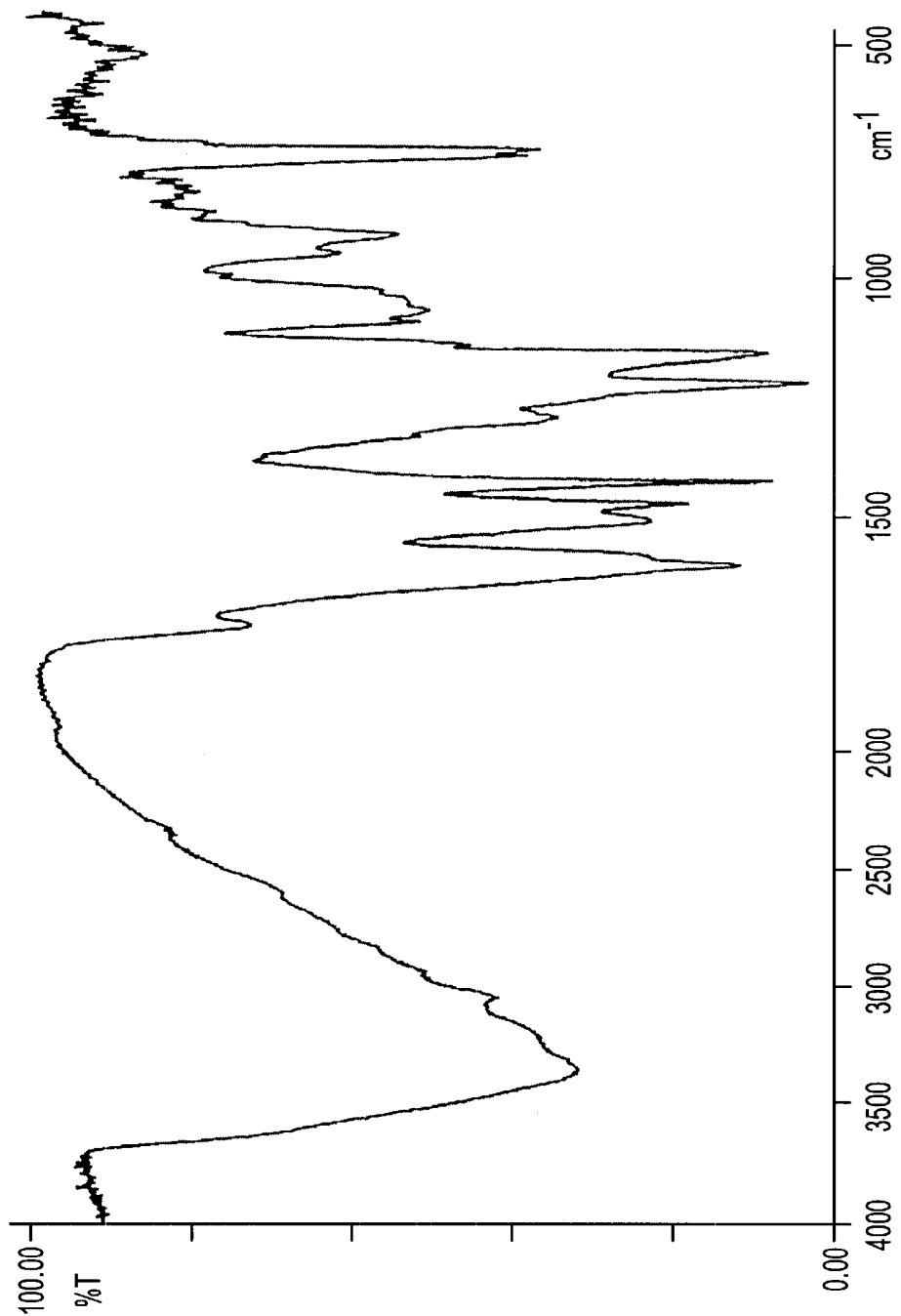
FIG. 1 is an infrared absorption spectrum (KBr) of the naphthol derivative obtained in Example 1-1.

In the specification and claims attached herewith, the term "lower" represents a group having 1–6 carbon atoms.

"Aromatic group" represents a 6-membered monocyclic aromatic group or condensed ring group consisting of up to 4 of 6-membered aromatic rings.

"Heterocyclic group having conjugated double bonds" represents a 5 or 6-membered monocyclic group or condensed ring group having at least one heteroatom selected from N, S and O and conjugated double bonds. When it consists a condensed ring group, said group may have up to 6 rings.

Examples of Z in the above general formula (2) include optionally substituted aromatic ring groups such as benzene, naphthalene and anthraquinone rings, and heterocyclic groups having conjugated double bonds such as thiophene, furan, pyrrole, imidazoline, pyrazole, isothiazole, isoxazole, pyridine, pyrazine, pyrimidine, pyridazine, triazole, tetrazole, indole, 1H-indazole, purine, 4H-quinolizine, isoquinoline, quinoline, phthalazine, naphthyridine, quinoxaline, quinazoline, cinnoline, pteridine and benzofuran. Examples of the groups represented by the general formula (2) include benzoxazole, benzothiazole and benzimidazole.

Examples of substituents for those groups include halogen atom, halogenated lower alkyl, nitro, lower alkyl, lower alkoxy such as methoxy, cyano, phenoxy, amino, pyrimidylamino, benzoylamino, sulphonic acid, hydroxy, esterified carboxyl such as alkoxycarbonyl and phenoxy carbonyl, amidaded carboxyl such as phenylaminocarbonyl, alkylamino sulfonyl and C2–6 alkenyl which may have an aryl. When said substituent contains an aromatic group, said aromatic ring may have further one or more substituents such as halogen atom, lower alkyl, lower alkoxy, phenyl and cyano groups.

In the naphthol derivative of the present invention represented by general formula (1), at least one of $Y_1$ and $Y_2$ is a group represented by general formula (2). When one of them is formula (2), the other may be, for example, carboxyl, esterified carboxyl such as phenoxy carbonyl and alkoxy carbonyl, and amidaded carboxyl such as aminoalkyl carbonyl, naphthylamino carbonyl and phenylamino carbonyl groups. The aromatic and aliphatic groups contained in the above groups may optionally have further substituents such as halogen atom, halogenated lower alkyl, nitro, lower alkyl, lower alkoxy and cyano groups.

The naphthalene structure of the naphthalene derivative of the present invention represented by formula (1) may have substituent(s) represented by Q. Examples of the substituents include optionally branched alkyl or alkoxy groups having 1–6 carbon atoms, halogen atom, nitro and nitroso groups. The number of the substituents represented by "m" is usually 0 and may be up to 3.

Examples of R include hydrogen atom, alkaline metal, optionally branched and optionally substituted alkyl and acyl groups each having 1–20 carbon atoms and phenylalkyl group.

The naphthol derivative of the present invention represented by general formula (1) may be prepared according to the scheme shown below:

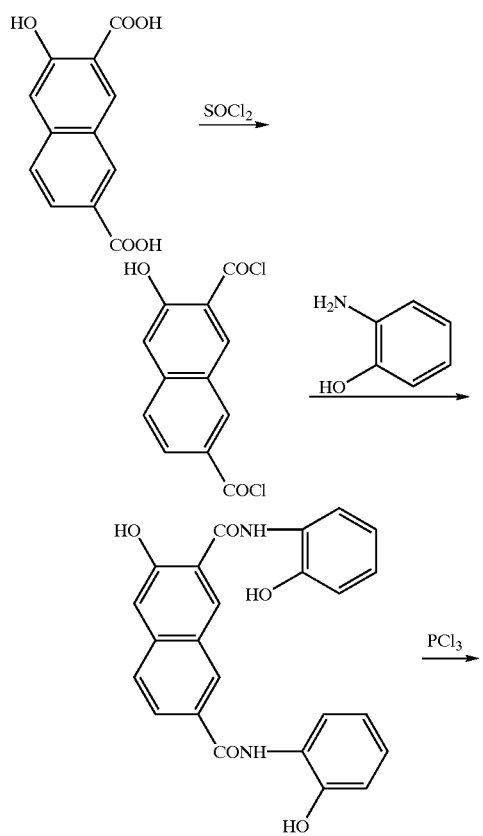

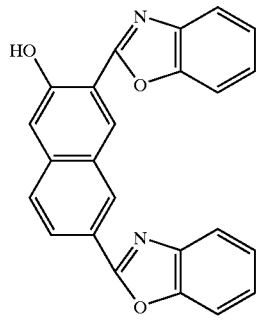

2-hydroxynaphthalene-3,6dicarboxylic acid is suspended in sulfolane. N,N-dimethyl formamide is added to the dispersion, and the mixture is reacted with thionyl chloride. Excess thionyl chloride is then removed from the reaction by distillation and a compound suitable for desired heterocyclic group is added to the reaction. Said compound may be, for example, 2-aminophenol, 2-amino thiophenol, 2-amino-4-nitrophenol, 2-amino-5nitrophenol, 2-amino-4-chloro-5-nitrophenol, 2-amino-4-chlorophenol, 2-amino-4methylphenol, 2-amino-3-hydroxypyridine, 2-amino-3hydroxynaphthalene, 2-amino-3-hydroxy anthraquinone, 2-amino-5methylphenol, 1-amino-2-hydroxynaphthalene, 2-amino-1-hydroxynaphthalene, o-phenylenediamine, 4-methoxy-1,2-phenylenediamine, 4-nitro-1,2-phenylenediamine, 4-chloro-1,2-phenylenediamine or 4,5-dichloro-1,2-phenylenediamine.

Then, phosphorus trichloride or phosphorus oxychloride is added to the mixture and the mixture is reacted at 50–180° C., preferably 50–140° C. The reaction mixture is then poured into water and the insoluble component is corrected by filtration to give the desired naphthol derivative having heterocyclic ring moiety.

Alternatively, the desired derivative may be prepared without thionyl chloride. In this embodiment, sulfolane solution of 2-hydroxynaphthalene-3,6-dicarboxylic acid and a 2-aminophenol derivative is added and reacted with phosphorus trichloride or phosphorus oxychloride to give the similar derivative.

2hydroxynaphthalene-3,6dicarboxylic acid used herein may be prepared by any known method. For example, a method disclosed in WO98/17621 comprising the step of reacting β-naphthol and carbon dioxide, aciding out the reaction mixture and, when desired, purifying the resulting compound, may be employed.

The naphthol derivatives of the present invention are useful as coupler components for azo compounds such as pigments or dyes. Said derivatives are also useful as charge generating materials of an organic photosensitive materials or as structural components of EL (electroluminescent) devices.

The present invention further provides monoazo, bisazo and trisazo compounds, which can be synthesized with the naphthol derivatives of general formula (1) or salts thereof.

The monoazo compound of the present invention is represented by general formula (3):

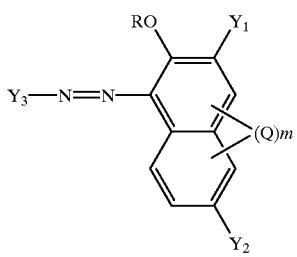
(3)

wherein $Y_1$, $Y_2$, Q, m and R are the same as defined above, $Y_3$ is an optionally substituted aromatic group.

In the general formula (3), $Y_3$ represents an optionally substituted aromatic group and is preferably, phenyl, naphthyl, anthryl, anthraquinonyl or pyrenyl group. The substituents may be the same as those disclosed in the definition of Z.

The monoazo compound of the present invention may be prepared by diazotizing an aromatic primary amine in an acidic solution with sodium nitrite or the like, and coupling the resulting aromatic diazonium compound with the above-described naphthol derivative. The coupling reaction is preferably carried out under weak alkaline condition since the reaction is significantly affected with the pH of the reaction solution. In addition, the reaction is preferably effected at the temperature where the aromatic diazonium salt will not be decomposed, usually, as low as 0–10 ° C.

Examples of the primary aromatic amines used herein may include the compounds well known in this field such as aniline, aminonaphthalene and substituted compounds thereof such as aniline derivatives having a substituent such as lower alkyl, halogen atom, nitro, hydroxy, carboxyl and sulfone groups. Preferred examples include aniline, aminonaphthalene, 6amino-m-toluenesulfonic acid, 2-amino-5-chloro-p-toluenesulfonic acid, 2-amino4-chlorobenzoic acid, 6-amino-4-chloro-m-toluenesulfonic acid, 5amino-2-chlorobenzenesulfonic acid and 2-aminonaphthalene-1-sulfonic acid.

The present invention also provide a bisazo compound of general formula (4):

$$A_1—N=N—L—N=N—A_2 \quad (4)$$

wherein $A_1$ and $A_2$ may be the same or different and each represents a group represented by general formula (5):

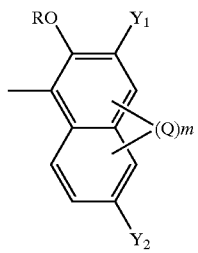
(5)

Wherein $Y_1$, $Y_2$, Q, m and R are the same as defined above;

L is selected from the group consisting of an optionally substituted arylene and groups represented by general formulae (6) and (7):

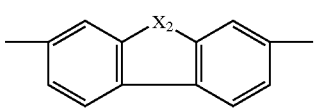
(6)

wherein $X_2$ is >NH—$CH_3$, >C=O or >C=S, $$—Ar—M—Ar'— \quad (7)$$

wherein each

Ar and Ar' is independently an optionally substituted arylene or heterocyclic group having conjugated double bonds;

M is selected from the group consisting of single bond, —$CH_2$—, —CH=C($Y_4$)— (wherein $Y_4$ is hydrogen or halogen atom, lower alkyl or cyano group), —O—, —S—, —S—S—, —CO—, —COO—, —$SO_2$—, —N($Y_5$)— (wherein $Y_5$ is an optionally substituted phenyl or lower alkyl group), —N=N—, —CH=CH—G—CH=CH— (wherein G is an arylene group) and a group of formula (8)

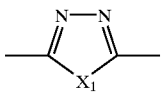
(8)

wherein $X_1$ is defined as above.

The substituents which may be directly attached to the arylene or heterocyclic group may be the same as those described in the definition of Z.

Examples of L are as follows:

(1) When L is an optionally substituted arylen group, preferred examples of L may include optionally substituted phenylene, naphthylene and anthlylene groups.

(2) When L is the group of formula (6), preferred examples of L may include

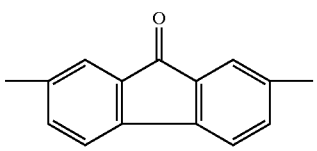

and

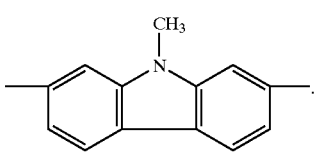

(3-1) When L is the group of formula (7) —Ar—M—Ar'— wherein M is a single bond, preferred examples include:

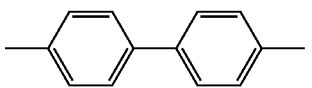

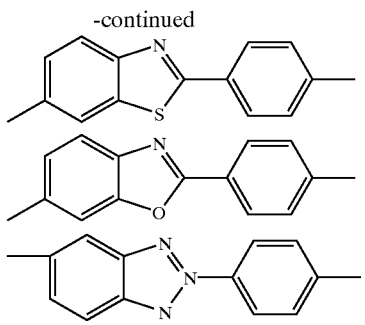

(3-2) wherein M is —CH$_2$—, preferred example of L may be

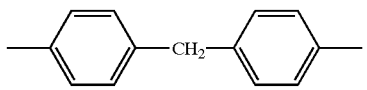

(3-3) wherein M is —CH=C(Y$_4$) (wherein Y$_4$ is hydrogen or halogen atom, lower alkyl or cyano group), preferred examples of L may include

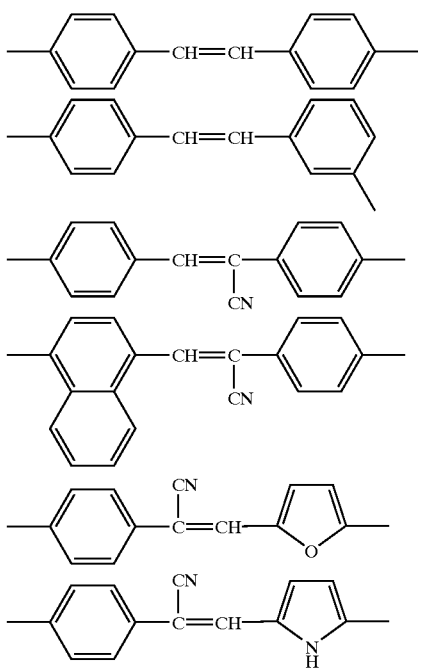

(3-4) wherein M is selected from the group consisting of —O—, —S—, —S—S—, —CO—, —COO—, —SO$_2$—, —N(Y$_5$)— (wherein Y$_5$ is an optionally substituted phenyl or lower alkyl group) and —N=N—, preferred examples of L may include

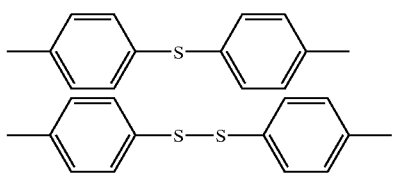

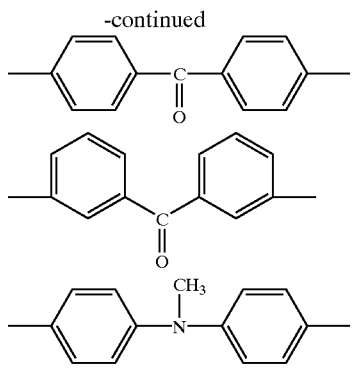

(3-5) wherein M is —CH=CH—G—CH=CH— (wherein G is an arylene group), preferred examples of L may include:

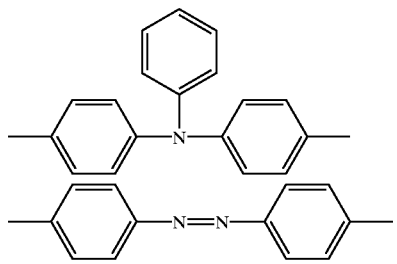

(3-6) wherein M is a group of the formula (8), preferred examples of L may include

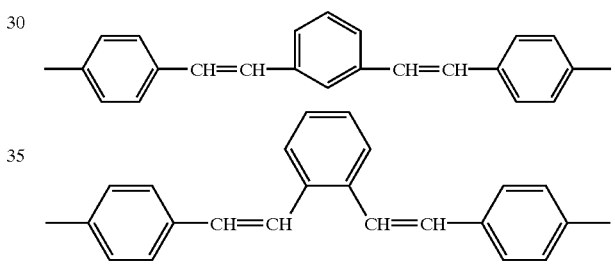

The bisazo compound of the present invention represented by general formula (4) may be prepared by diazotizing a diamine of general formula (13) with sodium nitrite or the like to give a tetrazonium compound, and coupling the same with the naphthol derivative of the present invention represented by general formula (1). Said coupling reaction may be carried out by dissolving fluoborate of said tetrazonium compound and a naphthol derivative of general formula (1) or a salt thereof in a solvent such as N,N-dimethylformamide or N-methyl-2-pyrrolidone, and additing sodium acetate or the like thereto.

$$H_2N-L-NH_2 \qquad (13)$$

wherein L is defiened as above.

In a further embodiment, the present invention provides a trisazo compound represented by general formula (9)

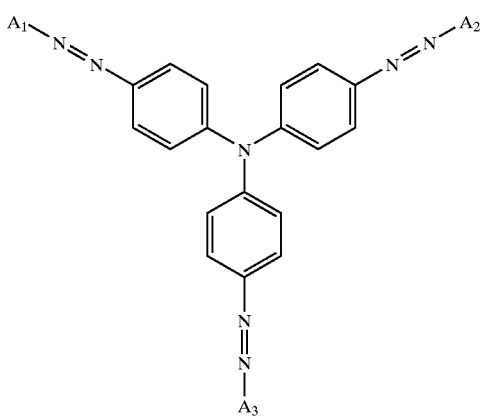

(9)

wherein $A_1$, $A_2$ and $A_3$ may be the same or different and each of them is the group represented by the general formula (5).

The trisazo compound of the present invention may be prepared as following procedure. That is, by diazotizing 4,4'4"-triamino triphenylamine of formula (10)

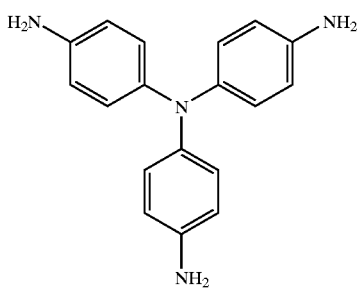

(10)

with, for example, hydrochloric acid and sodium nitrite to give a hexazonium salt of general formula (14):

(14)

wherein $X^-$ represents an anionic functionality.

Then, the resulting compound is coupled with a naphthol derivative of general formula (1) or a salt thereof to give desired trisazo compound. Said coupling reaction may be carried out by dissolving fluoborate of said hexazonium compound and a naphthol derivative of general formula (1) or a salt thereof in a solvent such as N,N-dimethylformamide or N-methyl-2-pyrrolidone, and additing sodium acetate or the like thereto.

The monoazo, bisazo and trisazo compounds of the present invention may be those prepared with 2 or more naphthol derivatives of the present invention, or those prepared with a mixed coupler composition consisting of at least one naphthol derivative of the present invention and any coupler component other than the same.

Thus obtained monoazo, bisazo and trisazo compounds of the present invention having heterocyclic moieties represent good light and thermal stability. Especially, the trisazo compound represents superior spectral characteristics than the other monoazo or bisazo compounds because of the expanded conjugated system in the structure, and therefore, may preferably be used as a charge generating material of an organic photosensitive material used in electrophotographic systems or laser printer systems.

Further, the monoazo, bisazo and trisazo compounds of the present invention may preferably be employed for manufacturing pigments, inks, paints, dyes, colorant for polymer compositions and the like.

The present invention further provides metal complexes comprising the naphthol derivatives of the present invention as ligands. Said metal complexes are those shown by general formulae (11) and (12).

(11)

(12)

wherein $Y_2$, $X_1$, Q, m and Z are the same as defined above, "Metal" represents a metal atom.

The general formulae (11) and (12) show metal complexes of which ligands are the naphthol derivative of general formula (1) wherein $Y_1$ is the group formula (2).

The metal center of the metal complex may be a metal atom which belongs in group 1B, 2B, 3 or 8 of the periodic table. Examples of preferable metal centers include copper, zinc, cobalt, nickel, iron, aluminum, yttrium, lanthanum and cerium.

When preparing the metal complex of the present invention, the metal atoms are usually provided as salts thereof. The salts are not specifically limited and may preferably be acetates, carbonates, sulfates or hydrochlorides. Acetates are especially preferable because of the good solubility and easiness in removing the side products from the reaction.

When the metal is copper, zinc, cobalt or nickel, the ratio of the metal to the naphthol derivative may preferably be 1:2; in case the metal is iron, aluminum, yttrium, lanthanum or cerium, the ratio of the metal to the naphthol derivative may preferably be 1:3.

The metal complex of the present invention may be prepared by dissolving a naphthol derivative of general formula (1) wherein Y, is general formula (2), in a suitable solvent, such as 1,4-dioxane, and adding thereto a metal salt such as copper acetate monohydrate, zinc acetate monohydrate or cobalt acetate tetrahydrate.

The metal complex of the present invention may be employed as a structural component of an electroluminescent (EL) device. The EL device prepared with the metal complex of the present invention is self-luminous and is EL device, which is driven with lower driven voltage. By employing the metal complex of the present invention, it becomes easy to prepare a multi color EL device, as a device with improved mechanical strength as well as a thinner film EL device.

The present invention will be further illustrated by the following examples.

EXAMPLES OF PREPARATION OF THE NAPHTHOL DERIVATIVES

EXAMPLE 1-1

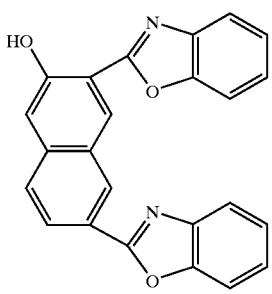

11.6 g of 2-hydroxy-3,6-dihydroxycarbonyl naphthalene was dispersed in 100 g of sulfolane, and 0.3 g of N,N-dimethylformamide then 36.0 g of thionyl chloride were added thereto. The mixture was reacted at 70° C. for 3 hours. After the reaction, the excess thionyl chloride was distilled off and 13.0 g of 2-aminophenol was added to the reaction mixture and the mixture was reacted at 80° C. for 5 hours. After that, 13.8 g of phosphorus trichloride was added and the mixture was reacted at 120–130° C. for 1 hour. After the reaction, the reaction mixture was poured in 400 g of water. Precipitates were collected by filtration, washed well with water and methanol, and dried to give 17.8 g of light yellow powder of the desired compound (melting point: 293° C., decomposition point: 341° C., FD-MS:m/z 378). The infrared spectrum (by KBr method) of the compound is shown in FIG. 1.

EXAMPLE 1-2

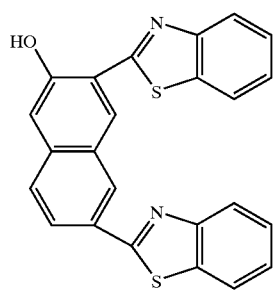

Figure 2:
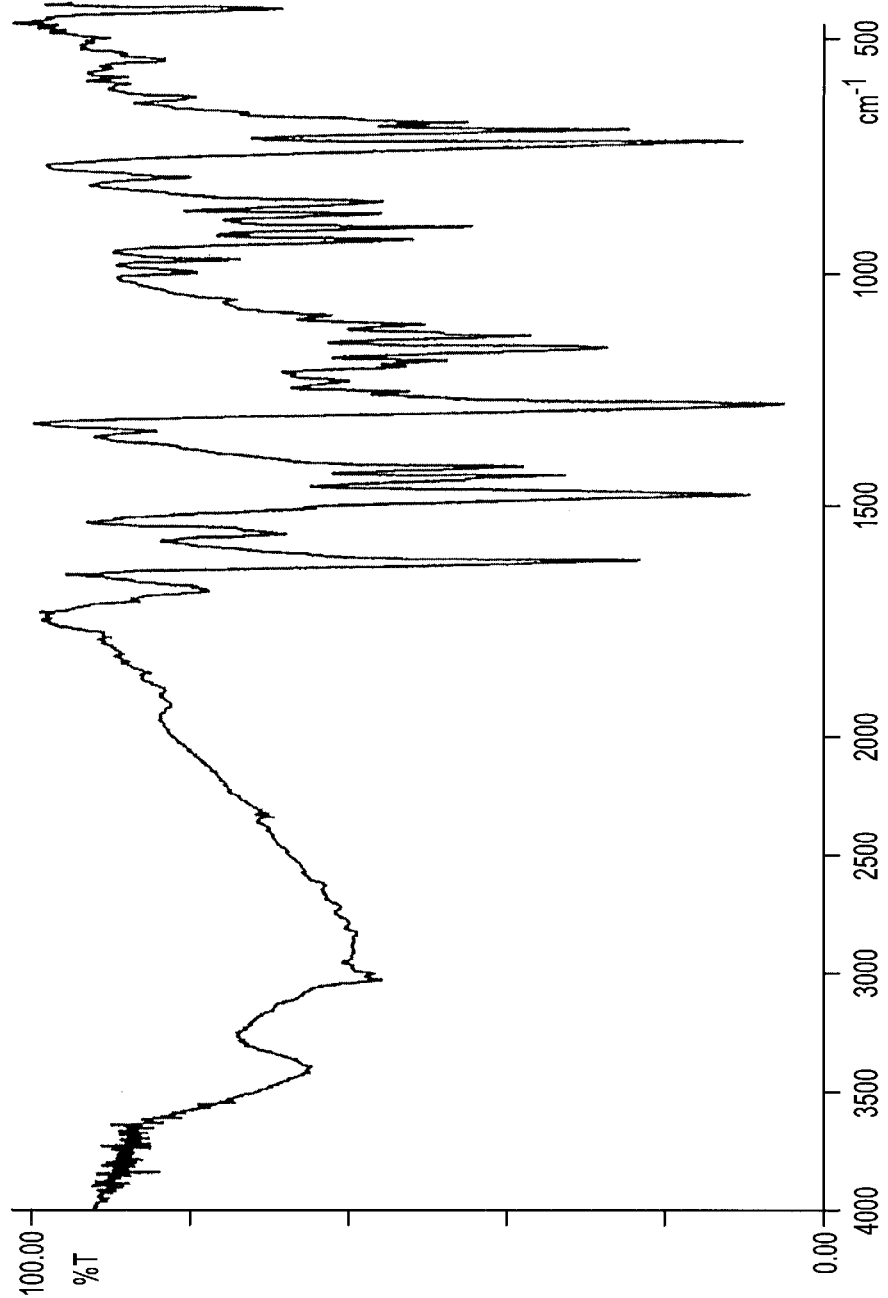
FIG. 2 is an infrared absorption spectrum (KBr) of the naphthol derivative obtained in Example 1-2.

According to the same manner as described in Example 1-1 with the exception that 14.9 g of 2-aminothiophenol was used instead of 2-aminophenol, 18.3 g of yellow powder of the desired compound was obtained (melting point: 264° C., decomposition point: 404° C., FDMS:m/z 410). The infrared spectrum (by KBr method) of the compound is shown in FIG. 2.

EXAMPLE 1-3

The compound of example 1-2 was prepared via another route. 2.32 g of 2-hydroxy-3,6-dihydroxycarbonylnaphthalene and 3.0 g of 2-aminothiophenol were dispersed in 40 g of sulfolane and 2.8 g of phosphorus trichloride was added thereto. The mixture was heated to 120° C. for 2 hours. The dispersion was once dissolved with increasing of the temperature and then, precipitated with progressing of the reaction. After cooling, precipitates were collected by filtration, washed well with water and methanol, and dried to give 3.2 g of yellow powder of the desired compound.

EXAMPLES 1-4–1-14

Oxazole derivatives were synthesized according to the same manner as described in Example 1-3 with the exception that aminophenol derivatives shown in table 1 were used instead of 2-aminothiophenol. Melting and decomposition points, and mass spectroscopic data of thus synthesized oxazole compounds are shown in Table 1.

TABLE 1
| Example No. | aminophenol | oxazole derivative | decomposition point | FD-MS · m/z |
|---|---|---|---|---|
| 1-4 | 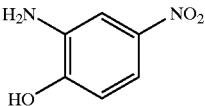 | 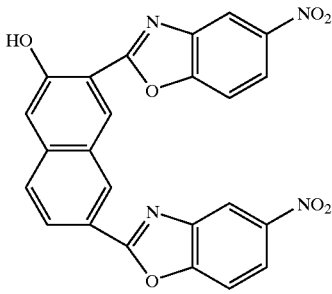 | 253° C. | 468 |
| 1-5 | 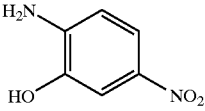 | 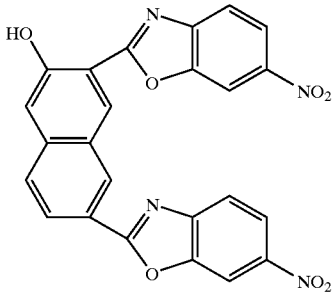 | 220° C. | 468 |
| 1-6 | 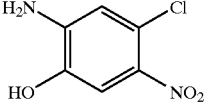 | 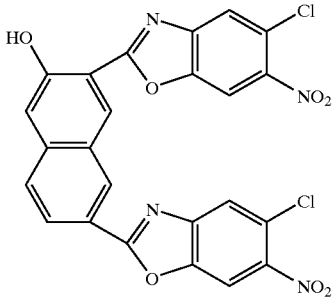 | 191° C. | 537 |
| 1-7 | 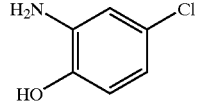 | 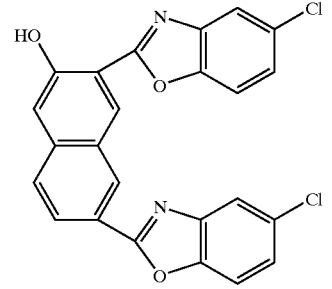 | 284° C. (melting point) 343° C. | 446 |

TABLE 1-continued
| Example No. | aminophenol | oxazole derivative | decomposition point | FD-MS · m/z |
|---|---|---|---|---|
| 1-8 | 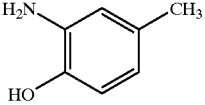 | 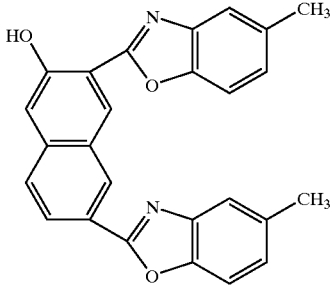 | 296° C. (melting point) 341° C. | 406 |
| 1-9 | 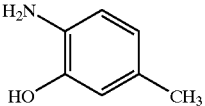 | 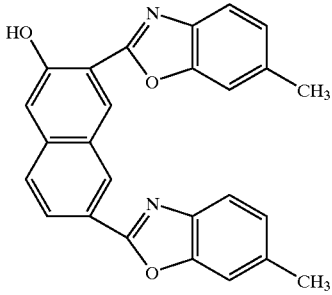 | 273° C. (melting point) 323° C. | 406 |
| 1-10 | 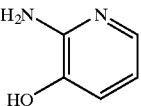 | 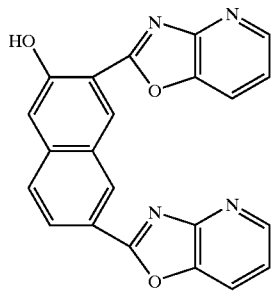 | 292° C. (melting point) 311° C. | 380 |
| 1-11 | 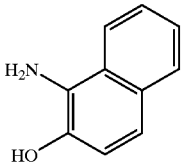 | 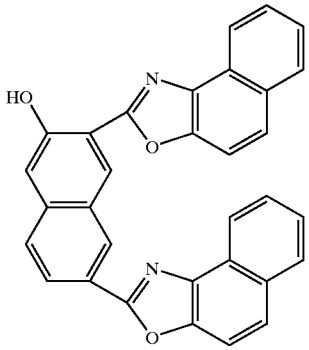 | 349° C. (melting point) 366° C. | 478 |

TABLE 1-continued

| Example No. | aminophenol | oxazole derivative | decomposition point | FD-MS · m/z |
|---|---|---|---|---|
| 1-12 | | | 249° C. (melting point) 370° C. | 478 |
| 1-13 | | | 316° C. (melting point) 323° C. | 478 |
| 1-14 | | | 212° C. | 638 |

EXAMPLE 1-15

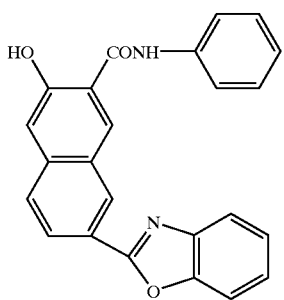

According to the same manner as described in Example 1-3 with the exception that 3.1 g of 2-hydroxy-6-hydroxycarbonyl-3-phenylaminocarbonyl naphthalene was used instead of 2-hydroxy-3,6-dihydroxycarbonyl naphthalene, 2,7 g of orange powder of the desired compound was obtained.

EXAMPLE 1-16

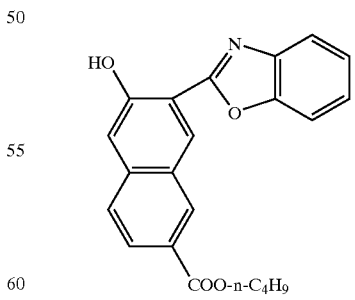

According to the same manner as described in Example 1-3 with the exception that 2.88 g of 2-hydroxy-3-hydroxycarbonyl-6-n-butoxycarbonyl naphthalene was used instead of 2-hydroxy-3,6-dihydroxycarbonyl naphthalene, 3.32 g of light yellow powder of the desired compound was obtained (melting point: 124° C., decomposition point: 289°

Figure 3:
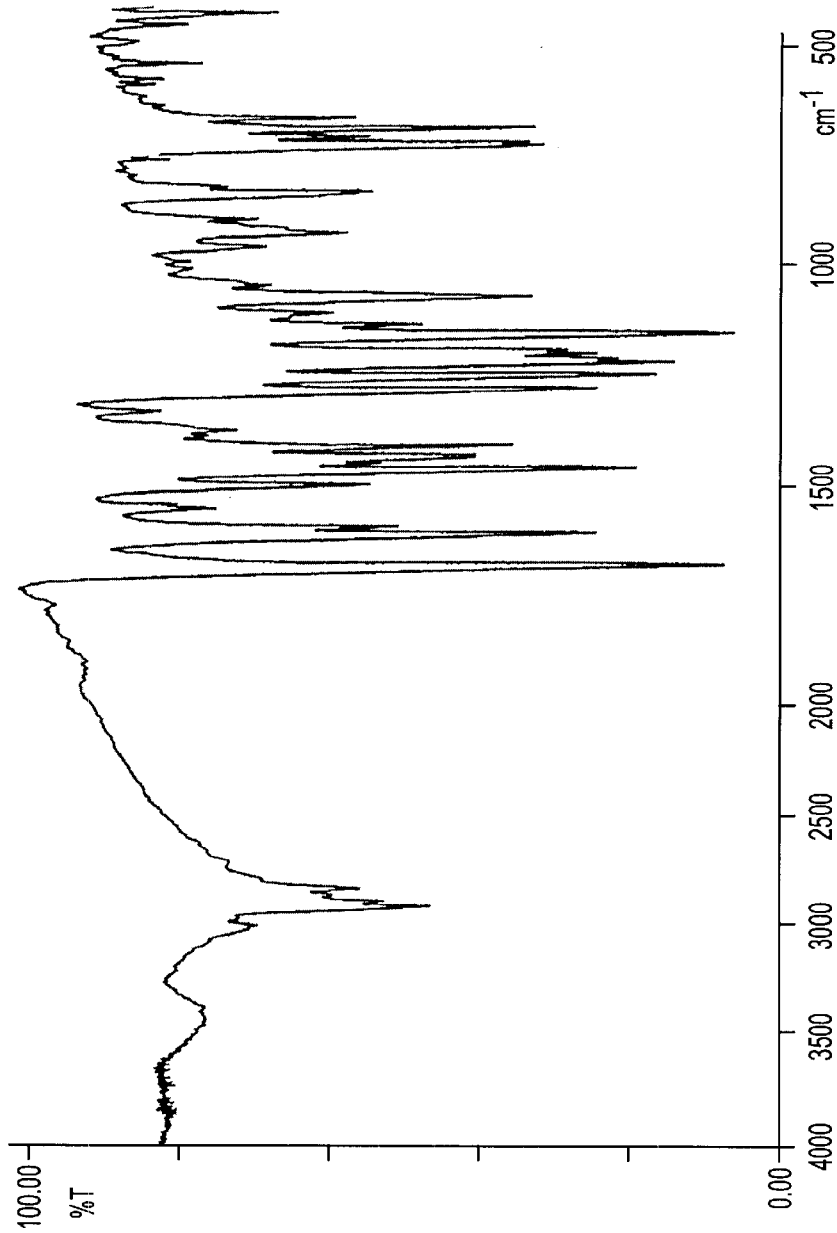
FIG. 3 is an infrared absorption spectrum (KBr) of the naphthol derivative obtained in Example 1-16.

C.). The infrared spectrum (by KBr method) of the compound is shown in FIG. 3.

EXAMPLES 1-17–1-25

Oxazole and thiazole derivatives were synthesized according to the same manner as described in Example 1-3 with the exception that 2,88 g of 2-hydroxy-3-hydroxycarbonyl-6-n-butoxycarbonyl naphthalene was used instead of 2-hydroxy-3,6-dihydroxycarbonylnaphthalene, and that aminophenols or aminothiophenols shown in table 2 were used respectively instead of 2-aminothiophenol. Melting and decomposition points of thus synthesized oxazole and thiazole compounds are shown in Table 2.

TABLE 2

| Example No. | aminophenol/ aminothiophenol | oxazole/thiazole derivative | decomposition point |
| --- | --- | --- | --- |
| 1-17 | [H₂N, HS-phenyl] | [benzothiazole-naphthalene-COO-n-C₄H₉] | 138° C. (melting point) 298° C. |
| 1-18 | [2-amino-3-hydroxypyridine] | [oxazolopyridine-naphthalene-COO-n-C₄H₉] | 289° C. |
| 1-19 | [H₂N, HO, NO₂-phenyl] | [nitro-benzoxazole-naphthalene-COO-n-C₄H₉] | 327° C. |
| 1-20 | [H₂N, HO, Cl, NO₂-phenyl] | [Cl, NO₂-benzoxazole-naphthalene-COO-n-C₄H₉] | 166° C. (melting point) 188° C. |

TABLE 2-continued

| Example No. | aminophenol/ aminothiophenol | oxazole/thiazole derivative | decomposition point |
| --- | --- | --- | --- |
| 1-21 | 2-amino-4-methylphenol | 5-methyl-benzoxazole coupled with hydroxy-naphthalene-COO-n-C₄H₉ | 143° C. (melting point) 271° C. |
| 1-22 | 1-amino-2-naphthol | naphtho[2,1-d]oxazole coupled with hydroxy-naphthalene-COO-n-C₄H₉ | 172° C. (melting point) 280° C. |
| 1-23 | 2-amino-1-naphthol | naphtho[1,2-d]oxazole coupled with hydroxy-naphthalene-COO-n-C₄H₉ | 302° C. |
| 1-24 | 3-amino-2-naphthol | naphtho[2,3-d]oxazole coupled with hydroxy-naphthalene-COO-n-C₄H₉ | 312° C. |
| 1-25 | 2-amino-3-hydroxy-anthraquinone | anthraquinone-fused oxazole coupled with hydroxy-naphthalene-COO-n-C₄H₉ | 283° C. (melting point) 302° C. |

EXAMPLE 1-26

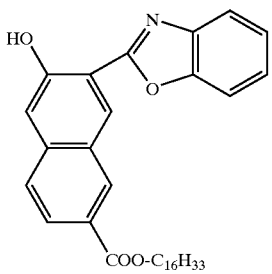

3.1 g of 3(benz-1',3'-oxazol-2'-yl)-2-hydroxy-6-n-butoxycarbonyl naphthalene was dissolved in 20 g of sulfolane and 20 g of n-hexadecanol and 0.31 g of sulfuric acid were added to the solution. The mixture was reacted at 150° C. for about 20 hours. During the reaction, n-butanol, generated from the reaction was adsorbed on molecular sieve. After the reaction, the reaction mixture was poured in 100 g of 50% aqueous methanol and precipitates were collected by filtration. The precipitates were washed with methanol to give 3.8 g of light yellow powder of the desired compound.

EXAMPLE 1-27

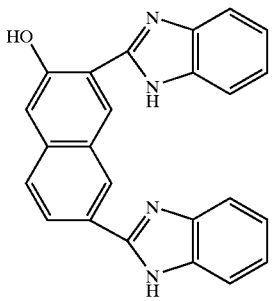

Figure 4:
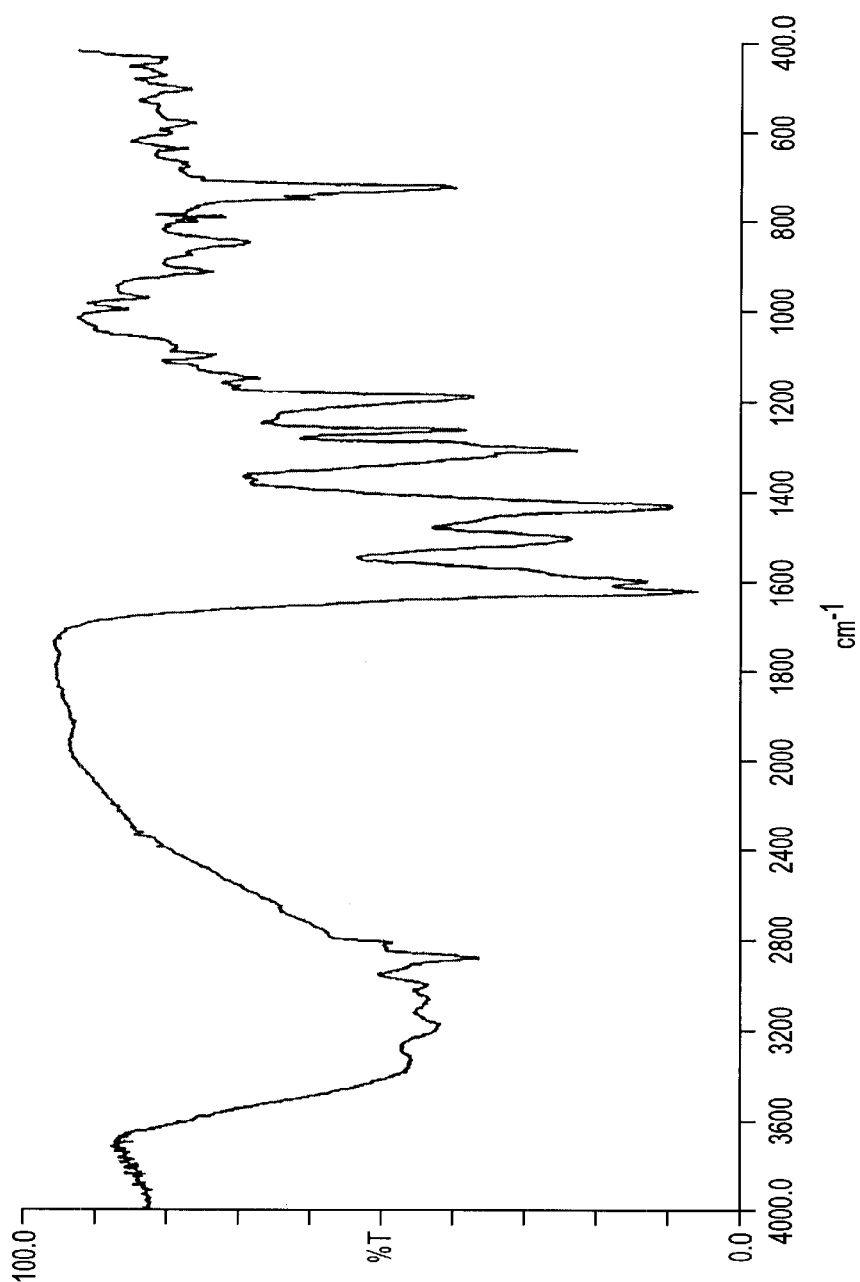
FIG. 4 is an infrared absorption spectrum (KBr) of the naphthol derivative obtained in Example 1-27.

2.5 g of 2-hydroxy-3,6-dihydroxycarbonyl naphthalene and 4.6 g of o-phenylenediamine were dispersed in 90 g of sulfolane, and 3.3 g of phosphorus oxychloride was added thereto. The mixture was reacted at 80° C. for 24 hours. Precipitates were collected by filtration, washed well with water and methanol, and then dissolved in 1,5-diazabicyclo[5.4.0]undeca-7-ene and stirred for 1 hour at 50–60° C. The reaction was developed in water and precipitates were collected by filtration and washed well with water and dried to give 2.1 g of yellow powder of the desired compound (MS:m/z (–) 375(MW=376.4)). The infrared spectrum (by KBr method) of the compound is shown in FIG. 4.

EXAMPLE 1-28

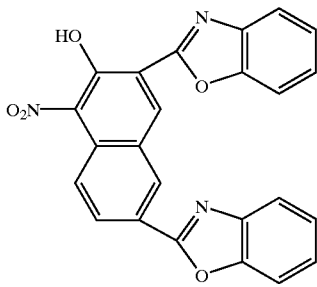

According to the same manner as described in Example 1-3 with the exception that 2.77 g of 2-hydroxy-3,6-dihydroxycarbonyl-1-nitronaphthalene was used instead of 2-hydroxy-3,6-dihydroxycarbonyl naphthalene, and that 2.70 g of aminophenol was used instead of 2-aminothiophenol, 3.31 g of brown powder of the desired compound was obtained (MS:m/z(–) 422 (MW=423.4)).

EXAMPLE 1-29

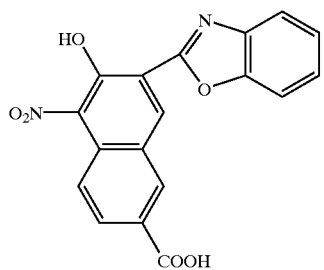

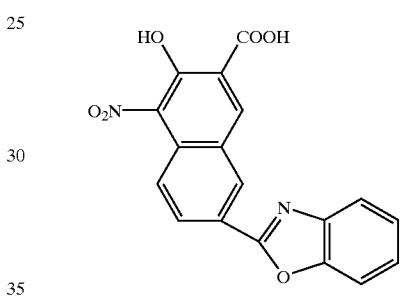

According to the same manner as described in Example 1-28 with the exception that the amount of 2-aminophenol was changed to 1.25 g, which is corresponding to the same molar amount of 2-hydroxy-3,6-dihydroxycarbonyl-1-nitronaphthalene added, 2.26 g of brown powder comprising the two desired compounds was obtained (MS:m/z(–) 350 (MW=350.3)).

EXAMPLE 1-30

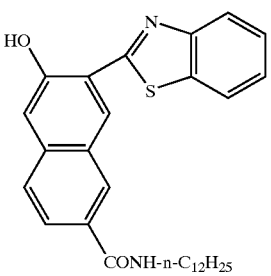

According to the same manner as described in Example 1-3 with the exception that 4.0 g of 2-hydroxy-6-n-dodecylaminocarbonyl-3-hydroxycarbonyl naphthalene was used instead of 2-hydroxy-3,6dihydroxycarbonyl naphthalene, 4.4 g of orange powder of the desired compound was obtained (melting point: 217° C., decomposition point: 330° C., MS:m/z(–) 487 (MW=488.7)).

EXAMPLE 1-31

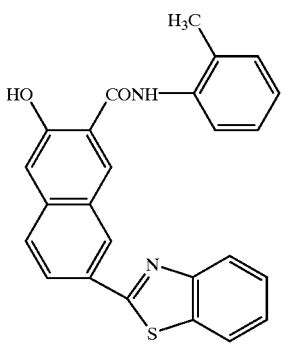

According to the same manner as described in Example 1-3 with the exception that 3.21 g of 2hydroxy-6-hydroxycarbonyl-3-(2'-tolylaminocarbonyl) naphthalene was used instead of 2-hydroxy-3,6-dihydroxycarbonyl naphthalene, 3.72 g of yellowish brown powder of the desired compound was obtained (melting point: 268° C., MS:m/z(–) 409 (MW=410.5)).

EXAMPLE 1-32

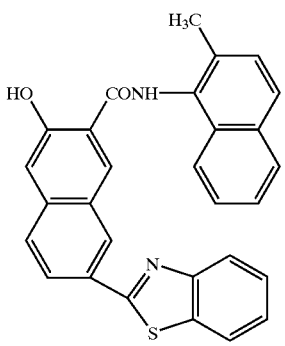

According to the same manner as described in Example 1-3 with the exception that 3.71 of 2-hydroxy-6-hydroxycarbonyl-3-(2'-methyl-1'-naphthyl aminocarbonyl) naphthalene was used instead of 2-hydroxy-3,6-dihydroxycarbonyl naphthalene, 4.23 g of yellow powder of the desired compound was obtained (melting point: 263° C., decomposition point: 330° C., MS:m/z(–) 459 (MW=460.6)).

EXAMPLE 1-33

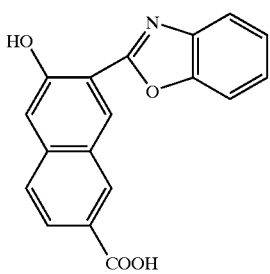

2.0 g of 2-hydroxy-6-n-butoxycarbonyl-3-(1',3'-benzoxazol-2'-yl) naphthalene obtained in Example 1-16 was dispersed in the mixture of 15 g of methanol and 15 g of water, and 0.3 g of sodium hydroxide was added thereto. The mixture was stirred at 80° C. for 3 hours. The precipitated sodium salt were collected by filtration and then were dispersed in 10 g of N,N-dimethylformamide. 0.8 g of 35% aqueous hydrochloric acid was added thereto and the mixture was stirred for about 1 hour. Precipitates were collected by filtration, washed well with water and dried to give 0.78 g of yellowish brown powder of the desired compound (decomposition point: 361° C., MS: m/z(–)304(MW=305.3)).

EXAMPLE 1-34

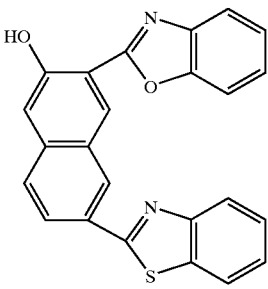

According to the same manner as described in Example 1-3 with the exception that 0.43 g of 2-hydroxy-6-hydroxycarbonyl-3-(1',3'-benzoxazol-2'-yl) naphthalene, which was obtained in Example 1-33, was used instead of 2-hydroxy-3,6-dihydroxycarbonyl naphthalene, 0.50 g of orange powder of the desired compound was obtained (decomposition point: 172° C., MS: m/z(–) 393 (MW=394.5)).

EXAMPLE 1-35

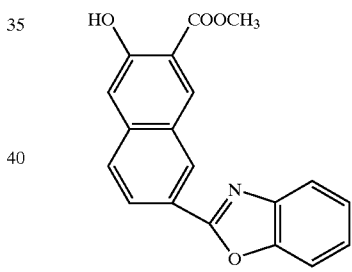

According to the same manner as described in Example 1-3 with the exception that 1.48 g of 2-hydroxy-6-hydroxycarbonyl-3methoxycarbonyl naphthalene was used instead of 2-hydroxy-3,6-dihydroxycarbonyl naphthalene, and that 0.79 g of 2-aminophenol was used instead of 2-aminothiophenol, 1.72 g of brown powder of the desired compound was obtained (melting point: 115° C., decomposition point: 388° C., MS: m/z(–) 318 (MW=319.3)).

EXAMPLE 1-36

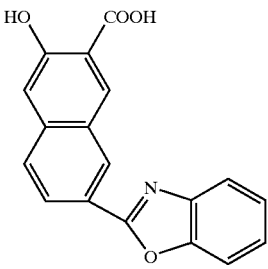

1.7 g of 2-hydroxy-3-methoxycarbonyl-6-(1',3'-benzoxazol-2'-yl) naphthalene obtained in Example 1-35 was dispersed in the mixture of 15 g of methanol and 15 g of water, and 0.3 g of sodium hydroxide was added thereto. The mixture was stirred at 80° C. for 3 hours. The precipitated sodium salt was collected by filtration and then were dispersed in 10 g of N,N-dimethylformamide. 0.8 g of 35% aqueous hydrochloric acid was added thereto and the mixture was stirred for about 1 hour. Precipitates were collected by filtration, washed well with water and dried to give 0.80 g of yellowish brown powder of the present invention (decomposition point: 282° C., MS: m/z(−) 304 (MW=305.3))

EXAMPLE 1-37

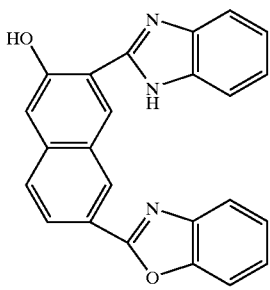

0.45 g of 2-hydroxy-3-hydroxycarbonyl-6-(1',3'-benzoxazol-2'-yl) naphthalene obtained in Example 1-36 and 0.31 g of o-phenylenediamine were dispersed in 20 g of sulfolane and 0.22 g of phosphorus oxychloride was added thereto. The mixture was heated to 80° C. for 24 hours. Precipitates were collected by filtration, washed well with water and methanol, and dried to give 0.44 g of yellowish brown powder of the desired compound (decomposition point: 171° C., MS: m/z(−) 376 (MW=377.4)).

EXAMPLE 1-38

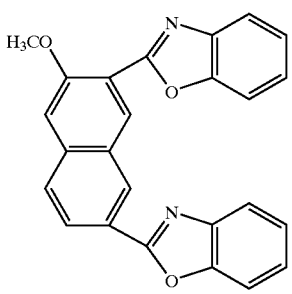

1.5 g of 2hydroxy-3,6-bis(1',3'-benzoxazol-2'-yl) naphthalene obtained in Example 1-1, 2.8 g of methyl iodide, 1.6 g of sodium carbonate and 0.1 g of polyethylene glycol (average molecular weight 4000) were dispersed or dissolved in 30 g of N,N-dimethylformamide, and the mixture was heated to 50° C. for 48 hours. The reaction mixture was then poured in 150 g of water and precipitates were collected by filtration, washed well with water and methanol, and dried to give 1.2 g of grayish brown powder of the desired compound (melting point: 227° C., MS: m/z (+) 393 (MW=392.4).

EXAMPLE 1-39

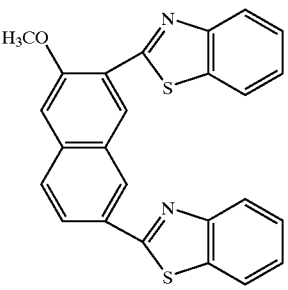

According to the same manner as described in Example 1-38 with the exception that 1.63 g of 2-hydroxy-3,6-bis(1',3'-benzothiazol-2'-yl)naphthalene obtained in Example 1-2 was used instead of 2hydroxy-3,6-bis(1',3'-benzoxazol-2'-yl) naphthalene, 1.31 g of yellowish brown powder of the desired compound was obtained (melting point: 235° C., MS: m/z(+) 425 (MW=424.5)).

EXAMPLE 1-40

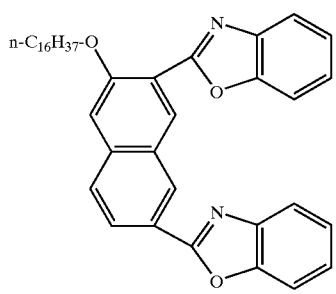

1.5 g of 2-hydroxy-3,6-bis(1',3'-benzoxazol-2'-yl) naphthalene obtained in Example 1-1, 1.6 g of octadecane bromide, 0.67 g of potassium carbonate and 0.1 g of polyethylene glycol (average molecular weight 4000) were dispersed or dissolved in 50 g of N,N-dimethylformamide, and the mixture was heated to 80° C. for 18 hours. The reaction mixture was then poured in 150 g of water and precipitates were collected by filtration, washed well with water and methanol, and dried to give 1.85 g of khaki powder of the desired compound (melting point: 115° C., MS: m/z (+) 632 (MW=630.9)).

EXAMPLE 1-41

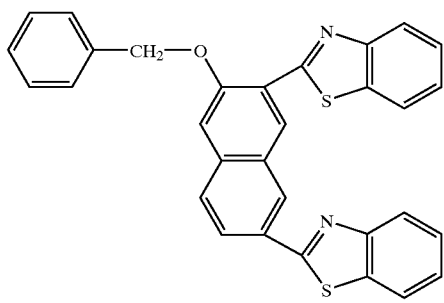

According to the same manner as described in Example 1-40 with the exception that 1.61 g of 2-hydroxy-3,6-bis(1', 3'-benzothiazol-2'-yl)naphthalene obtained in Example 1-2 was used instead of 2-hydroxy-3,6-bis(1',3'-benzoxazol-2'-yl) naphthalene, and that 0.62 g of benzyl chloride was used instead of octadecyl bromide, 1.83 g of yellow powder of the desired compound was obtained (melting point: 212° C., MS: m/z(+) 501 (MW=500.6)).

EXAMPLE 1-42

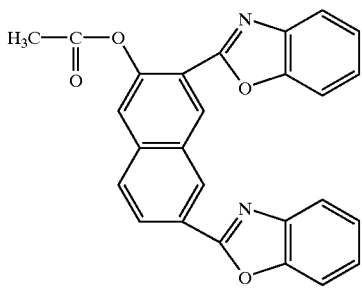

Figure 7:
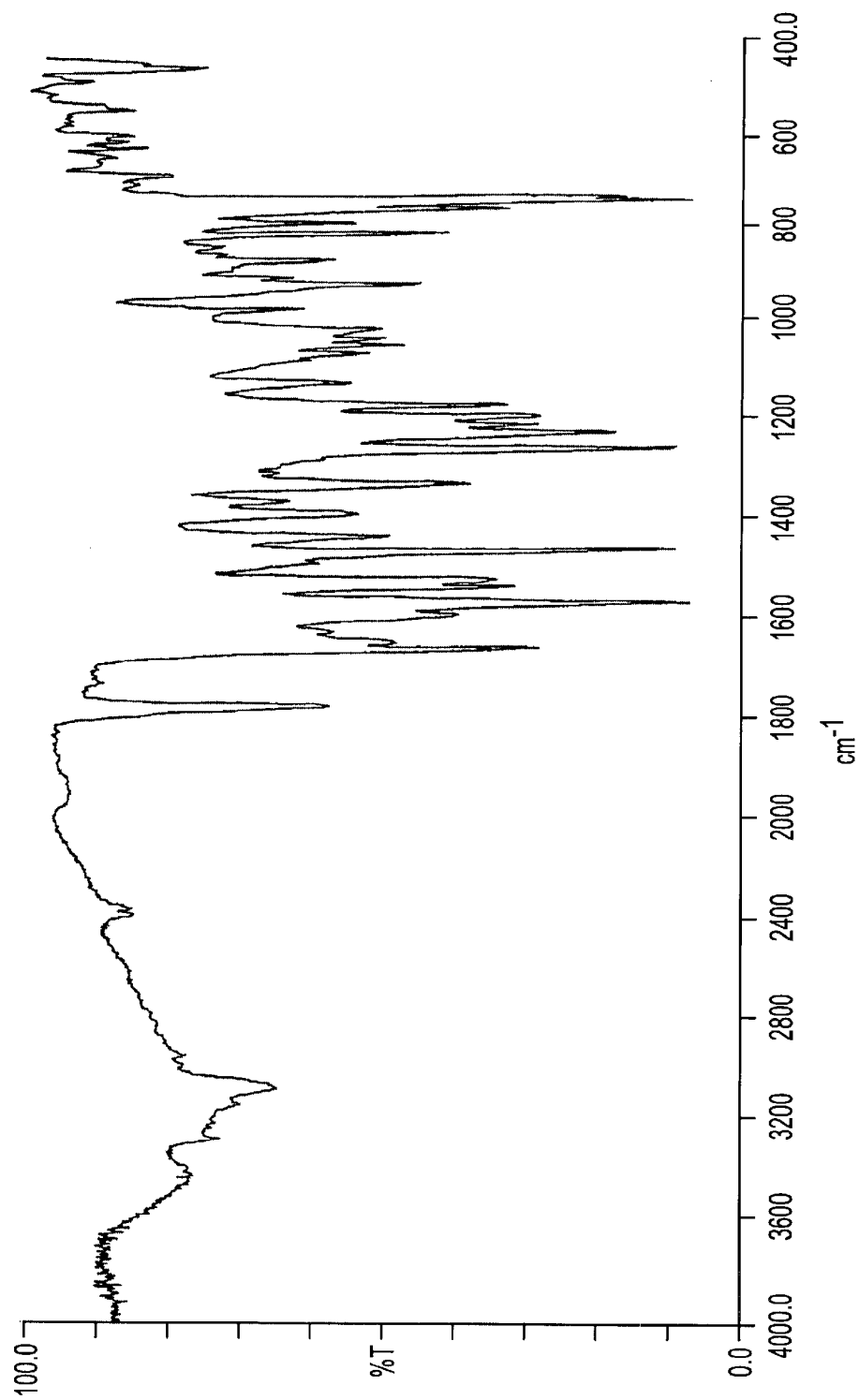
FIG. 7 is an infrared absorption spectrum (KBr) of the complex molecule obtained in Example 1-42.

1.0 g of 2-hydroxy-3,6-bis(1',3'-benzoxazol-2'-yl) naphthalene obtained in Example 1-1, 5.0 g of acetic anhydride, 5.0 g of acetic acid and 0.05 g of N,N-dimethyl-4-aminopyridine were mixed and the mixture was reacted at 100° C. for 10 hours. The reaction mixture was poured in 20 g of water and precipitates were collected by filtration. The precipitates were washed well with water and dried to give 0.92 g of orange powder of the desired compound (melting point: 244° C., MS: m/z(−) 419 (MW=420.4)). The infrared spectrum (by KBr method) of the compound is shown in FIG. 7.

EXAMPLE 1-43

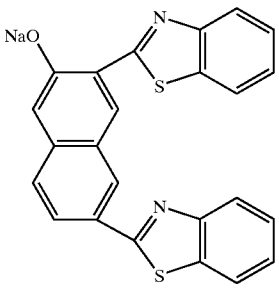

0.5 g of 2hydroxy-3,6-bis(1',3'-benzothiazol-2'-yl) naphthalene obtained in Example 1-2, 0.066 g of sodium methoxide, and 5.0 g of methanol were mixed and reacted at 50° C. for 5 hours. Precipitates were collected by filtration and dried to give 0.44 g of orange powder of the desired compound (Na content: 5.44 wt % (calculated 5.32 wt %), MS: m/z(−) 431 (MW=432.5)).

Synthesis of Monoazo Compounds

EXAMPLE 2-1

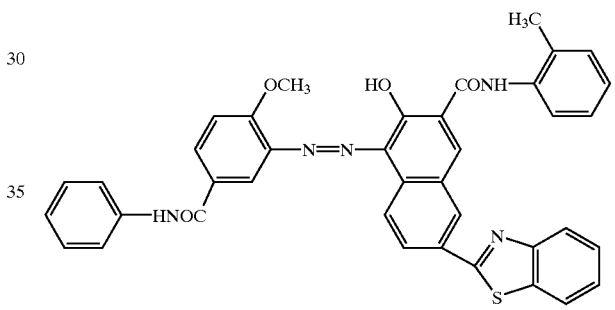

4.1 g of 2-hydroxy-3-o-tolylaminocarbony-6-(1',3'-benzothiazol-2'-yl)naphthalene obtained in Example 1-31 was dispersed in 80 g of N-methyl-2-pyrrolidone, and 1.2 g of sodium hydroxide was added thereto to dissolve and the solution was kept at 10–15° C.

Figure 5:
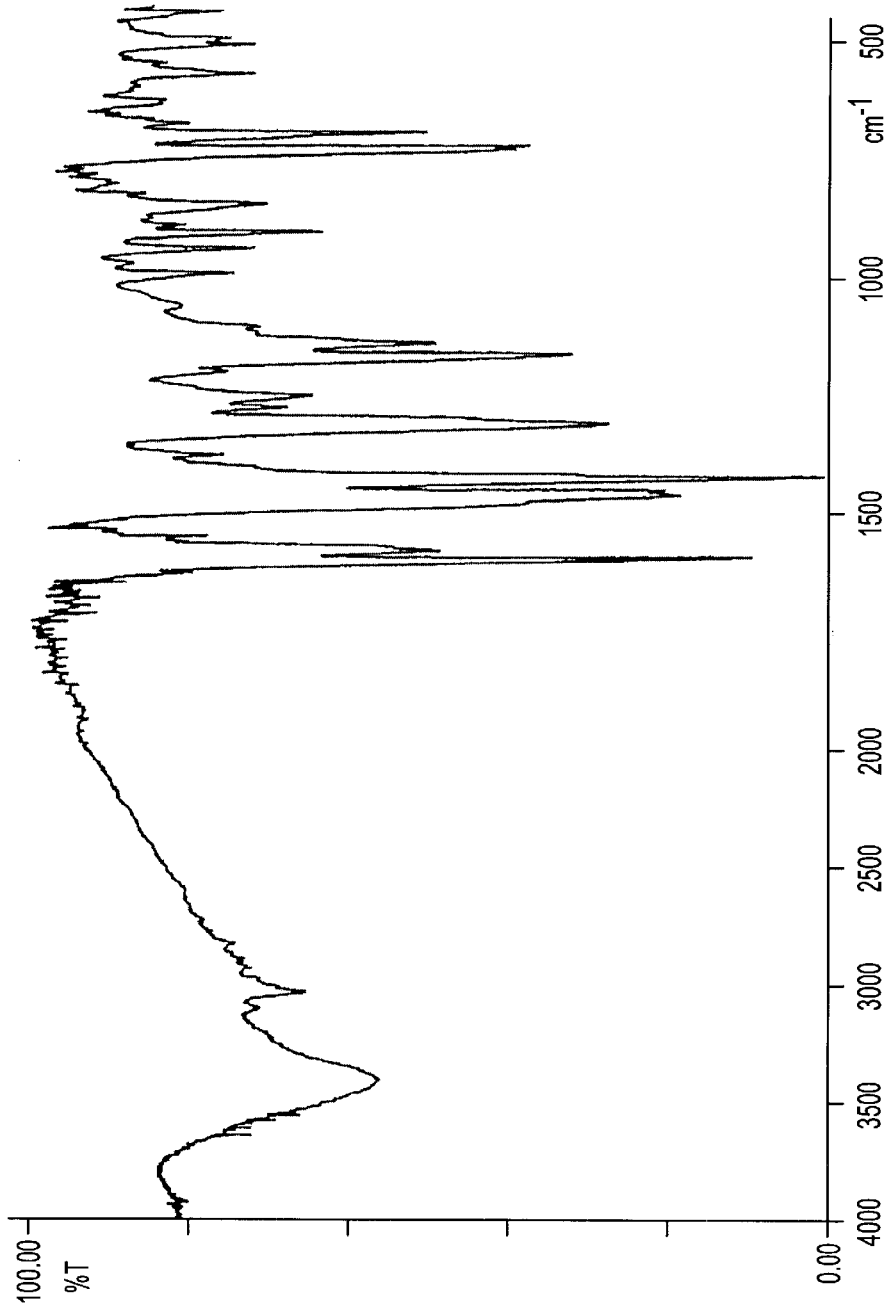
FIG. 5 is an infrared absorption spectrum (KBr) of the monoazo compound obtained in Example 2-1.

7.3 g of 2-methoxy-5-phenylaminocarbonyl aniline was dispersed in 100 g of water and was added with 4.0 g of 35% aqueous hydrochloric acid. The suspension was dissolved once and then became clouded gradually. After that, the mixture was kept at 0° C. and 2.3 g of sodium nitrite in water (10 g) was added dropwise to effect diazotization reaction. One hour after, insoluble matter was removed by filtration and 20 ml of 42% aqueous fluoroboric acid was added to the filtrate. The mixture was stirred for about 30 minutes and precipitates were collected by filtration to give yellow crystal. Thus obtained diazonium salt 5.1 g was added to the above-obtained solution and stirred for 3 hours at room temperature. Then, 80 g of water was added thereto and stirred about 1 hour. Precipitates were collected by filtration, washed well with water and methanol, and dried to give 6.1 g of reddish purple crystal of the desired compound (λmax= 542 nm, decomposition point: 314° C.). The infrared spectrum (by KBr method) of the compound is shown in FIG. 5.

EXAMPLE 2-2

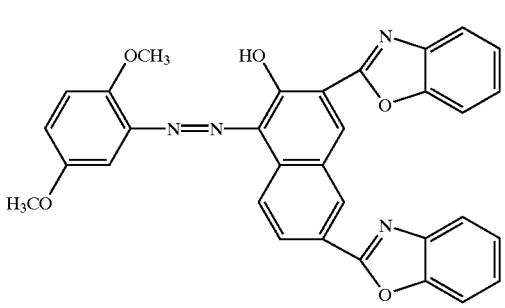

According to the same manner as described in Example 2-1 with the exception that 3.8 g of 2-hydroxy-3,6-bis(1',3'-benzoxazol-2'-yl)naphthalene obtained in Example 1-1 was used instead of 2hydroxy-3-o-tolylaminocarbonyl-6-(1',3'-benzothiazol-2'-yl)naphthalene, that 2,5- dimethoxyaniline was used instead of 2-methoxy-5-phenylaminocarbonyl aniline and that 31 g of its diazonium salt was added, 4.1 g of dark purple powder of the desired compound was obtained ($\lambda$max=543 nm, decomposition point: 313° C.),

EXAMPLE 2-3

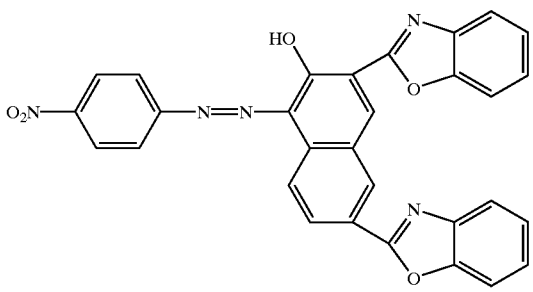

According to the same manner as described in Example 2-1 with the exception that 3.8 g of 2-hydroxy-3,6-bis(1',3'-benzoxazol-2'-yl)naphthalene obtained in Example 1-1 was used instead of 2-hydroxy-3-o-tolylaminocarbonyl-6-(1',3'-benzothiazol-2'-yl)naphthalene, that p-nitroaniline was used instead of 2-methoxy-5-phenylaminocarbonyl aniline and that 2.8 g of its diazonium salt was added, 3.8 g of reddish purple powder of the desired compound was obtained ($\lambda$max=634 nm, decomposition point: 345° C.).

EXAMPLE 2-4

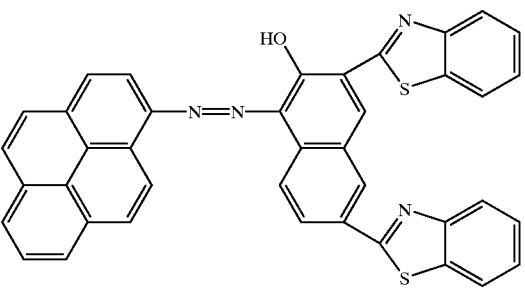

According to the same manner as described in Example 2-1 with the exception that 0.82 g of 2-hydroxy-3,6-bis(1', 3'-benzothiazol-2'-yl)naphthalene obtained in Example 1-2 was used instead of 2-hydroxy-3-o-tolylaminocarbonyl-6-(1',3'-benzothiazol-2'-yl)naphthalene, that 1.09 g of 1-aminopyrene was used instead of 2methoxy-5-phenylaminocarbonyl aniline and that 0.63 g of its diazonium salt was added, 0.66 g of bluey purple powder of the desired compound was obtained ($\lambda$max=617 nm, decomposition point:340° C.).

Synthesis of Bisazo Compounds

EXAMPLE 3-1

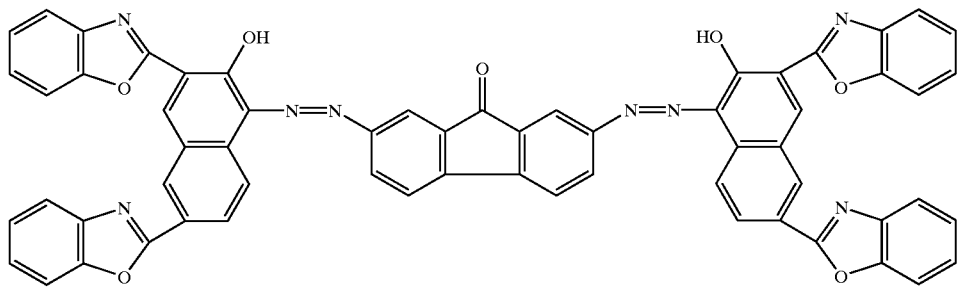

1.23 g of 2,7diamino-9-fluorenone was dispersed in 20 g of water, and dissolved by adding 1.5 g of 35% aqueous hydrochloric acid thereto. Then, the solution was kept at 0° C. and 0.73 g of sodium nitrite in water (5 g) was added dropwise to effect diazotization process. Then, 4 g of 42% fluoroboric acid was added and precipitated bisdiazonium salt (tetrazonium salt) was collected by filtration. On the other hand, 1.5 g of 2-hydroxy-3,6-bis(1',3'-benzoxazol-2-yl)naphthalene obtained in Example 1-1 was dissolved in 50 g of N-methylpyrrolidone, 0.5 g of sodium hydroxide was added thereto and then, the mixture was stirred well to dissolve and kept at 15° C. To thus obtained solution, 0.8 g of above-obtained tetrazonium salt was added and the mixture was stirred well more than one hour to effect coupling reaction. After that, 0.8 g of acetic acid was added thereto and then, 150 g of methanol were added gradually to the mixture. Precipitates were collected by filtration, washed well with water and methanol, and dried to give 1.6 g of dark bluey purple powder of the desired compound ($\lambda$max=514.5 nm, decomposition point: 334° C.).

EXAMPLE 3-2

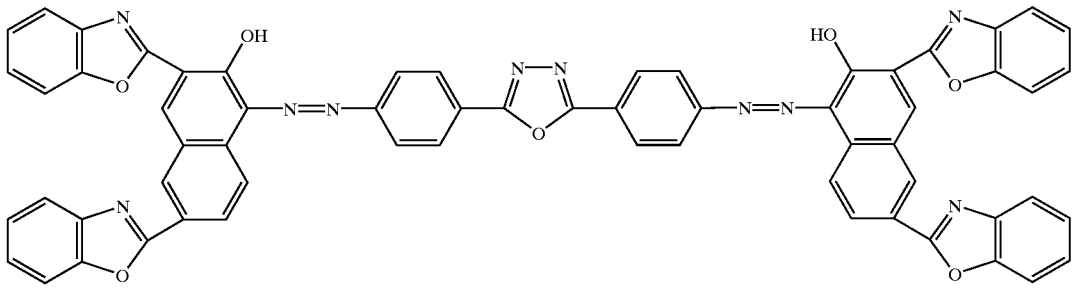

According to the same manner as described in Example 3-1 with the exception that 2.74 g of bis-2,5-(4'-aminophenyl)-1,3,4-oxadiazole was used instead of 2,7-diamino-9-fluorenone, 1.8 g of dark bluey purple powder of the desired compound was obtained (λmax=503.5 nm).

EXAMPLE 3-3

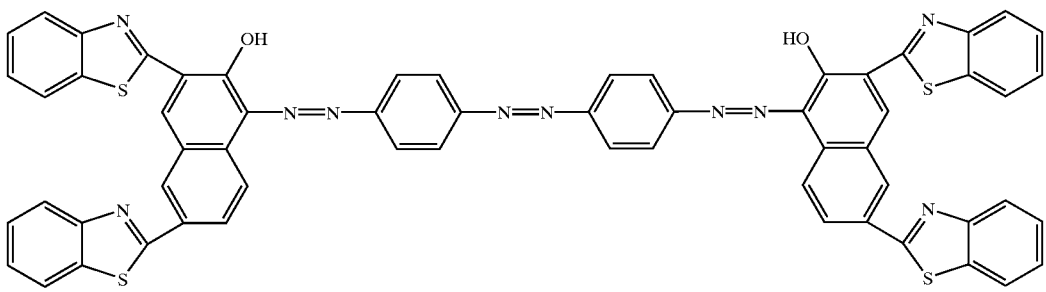

1.24 g of 4,4'-diaminoazobenzene was dispersed in 50 g of water and 4.0 g of 35% aqueous hydrochloric acid was added thereto to dissolve the mixture. The mixture was kept at 0° C. and added with 0.83 g of sodium nitrite in water (10 g) to effect diazontizing process. After that, insoluble matters were removed simultaneously with carbon treatment. The clear supernatant was added with 10 g of 42% aqueous fluoroboric acid and the precipitated bisdiazonium salt (tetrazonium salt) was collected by filtration.

On the other hand, 1.64 g of 2-hydroxy-3,6bis(1',3'-benzothiazol-2'-yl)naphthalene obtained in Example 1-2 was dispersed in 50 g of N-methyl-2-pyrrolidone, and added with 0.82 g of the above-obtained tetrazonium salt. The mixture was kept at 15° C. and added with 0.60 g of sodium acetate to effect coupling reaction. The mixture was stirred more than 5 hours and then added with 0.8 g of acetic acid. Precipitates were collected by filtration, washed well with water and methanol, and dried to give 1.76 g of dark bluey purple powder of the desired compound (λmax=683 nm, decomposition point: 345° C.).

Synthesis of Trisazo Compounds

EXAMPLE 4-1

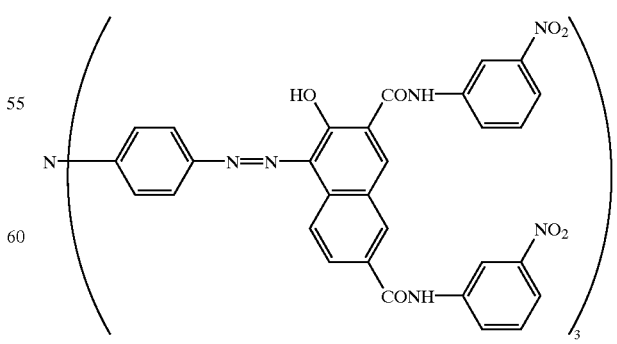

1.7 g of 4,4',4"-triaminotriphenylamine was dispersed in 25 g of water and was added with 30 g of 36% aqueous hydrochloric acid, and then the mixture was stirred at room temperature for about 30 minutes. After that, the mixture was cooled to 0–5° C. and added with 1.5 g of sodium nitrite in water (5 g) to effect diazotizing process. One hour after, insoluble matter was removed by filtration and 12 ml of 42% aqueous fluoroboric acid was added to the filtrate. The mixture was stirred for about 30 minutes and then, precipitated trisdiazonium salt (hexazonium salt) was collected by filtration to give yellowish brown crystal. Thus obtained hexazonium salt (0.6 g) and 1.659 of 2-hydroxy-3,6-bis-(3'-nitrophenylamino carbonyl)naphthalene were dissolved in 100 ml of N,N-dimethylformamide (DMF), 1.5 g of sodium acetate in water (15 ml) was added to the solution, and then, the mixture was stirred for about 3 hours at room temperature. The products were collected by filtration, washed well with DMF, water and methanol, and dried to give 1.42 g of black purple powder of the desired compound (decomposition point: 290.5° C.).

EXAMPLES 4-2–4-5

Trisazo compounds were synthesized according to the same manner as described in Example 4-1 with the exception that coupler components shown in table 3 were used instead of 2hydroxy-3,6-bis(3'-nitrophenylamino carbonyl) naphthalene. Decomposition points of thus synthesized trisazo compounds are shown in Table 3.

TABLE 3

| Example No. | coupler component | trisazo compound | color | decomposition point |
|---|---|---|---|---|
| 4-2 | Example 1-2 | | very dark purple | 289° C. |
| 4-3 | Example 1-5 | | very dark purple | 231° C. |
| 4-4 | Example 1-6 | | very dark purple | 230° C. |
| 4-5 | Example 1-7 | | very dark purple | 162° C. |

EXAMPLE 5-1
Photo-conductive Effect Test

One part by weight of azo compound obtained in Example 4-1 was mixed with one part by weight of polyvinyl butyral (S-Lec BH-3, Sekisui Chemical Co., Ltd.) and 10 parts by weight of cycdohexanone by means of ball mill. The obtained dispersion liquid of the azo compound was applied on a piece of aluminum sheet with bar coater and dried to give 5 μm thick charge generating layer. One part by weight of N-ethylcarbazole-3-aldehydediphenylhydrazone and one part by weight of polycarbonate resin (Panlite K-1285, Teijin Chemicals Ltd.) in 20 parts by weight of 1,2-dichloroethane were applied on thus obtained charge generating layer to give charge transporting layer about 20 μm thick. Thus a two layer type electrophotographic photoconductor was obtained.

The half decay exposure (E1/2) of thus obtained photoconductor was determined with Electrostatic Paper Analyzer (EPA-8100, Kawaguchi Electric Works Co., Ltd.). The photoconductor was charged in the dark by means of corona discharge at −5.0 kV, and then was exposed to white light at 20 lux to determine the amount of exposure required to decay the surface potential to half. Thus obtained half decay exposure (E1/2) was 8.81 lux·sec. In addition, the surface potential (i.e. residual potential) obtained after enough exposure (exposure to 200 lux·sec) was −2V.

In case of the azo compound obtained in Example 4-2 was used, the half decay exposure was 5.6 lux·sec and the surface potential (residual potential) after enough exposure (exposure to 200 lux·sec) was −2V.

Synthesis of Complexes

EXAMPLE 6-1

Figure 6:
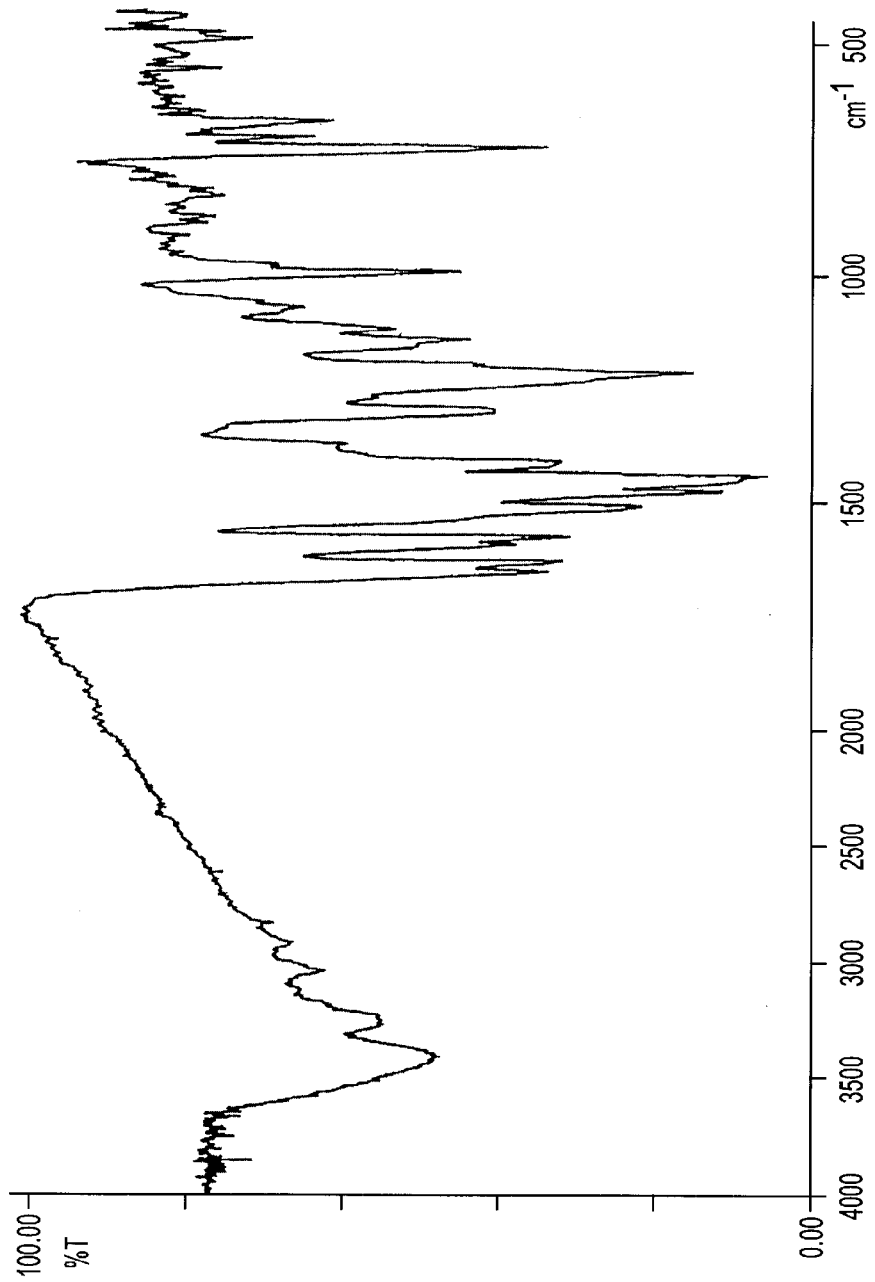
FIG. 6 is an infrared absorption spectrum (KBr) of the complex molecule obtained in Example 6-1.

0.41 g of 2-hydroxy-3,6-bis(1',3'-benzothiazol-2'-yl) naphthalene obtained in Example 1-2 was dissolved in 10 g of 1,4-dioxane and 0.1 g of copper acetate monohydrate in 10 g of 1,4-dioxane was added to the solution. The mixture was stirred and heated to 120° C. for 10–20 minutes by means of autoclave, and then, was cooled to room temperature. Precipitates were collected by filtration, washed with 1,4-dioxane, and dried to give 0.43 g of dark brown crystal of the copper complex (decomposition point: 309° C.). The measured value of copper content was 7.01% (calc. 7.2%). The Infrared spectrum (by KEr method) of the compound is shown in FIG. 6.

EXAMPLES 6-2–6-6

Metal complexes were synthesized according to the same manner as described in Example 6-1 with the exception that oxazole or thiazole compounds shown in table 4 were used instead of 2-hydroxy-3,6-bis(1',3'-benzothiazol-2'-yl) naphthalene, and that metal salts shown in Table 4 were used instead of copper acetate monohydrate. Decomposition points of thus synthesized metal complexes are shown in Table 4.

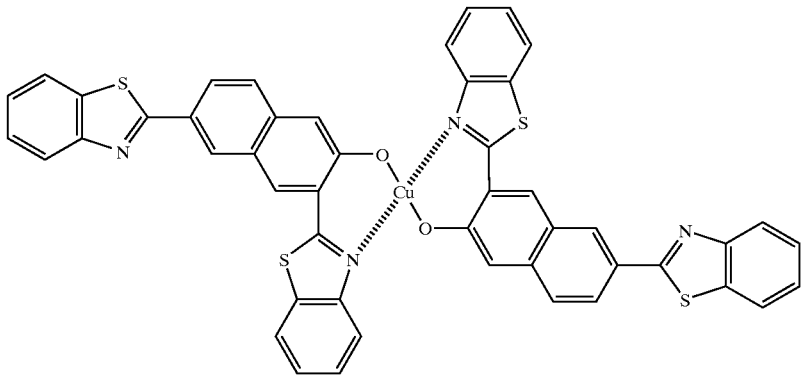

TABLE 4

| Example No. | oxazole/thiazole | metal salt | metal complex | decomposition point |
|---|---|---|---|---|
| 6-2 | | Cu(OAc)$_2$·H$_2$O | | 320° C. |
| 6-3 | | Cu(OAc)$_2$·H$_2$O | | 327° C. |
| 6-4 | | Zn(OAc)$_2$·H$_2$O | | 346° C. |

TABLE 4-continued

| Example No. | oxazole/ thiazole | metal salt | metal complex | decomposition point |
|---|---|---|---|---|
| 6-5 | (benzothiazole-naphthol with COO-n-C$_4$H$_9$ structure) | Co(OAc)$_2$·H$_2$O | (Co complex of two benzothiazole-naphtholate ligands with COO-n-C$_4$H$_9$ groups) | 383° C. |
| 6-6 | (anthraquinone-fused naphthoxazole-naphthol with COO-n-C$_4$H$_9$ structure) | Cu(OAc)$_2$·H$_2$O | (Cu complex of two anthraquinone-fused naphthoxazole-naphtholate ligands with COO-n-C$_4$H$_9$ groups) | 368° C. |

EXAMPLE 6-7

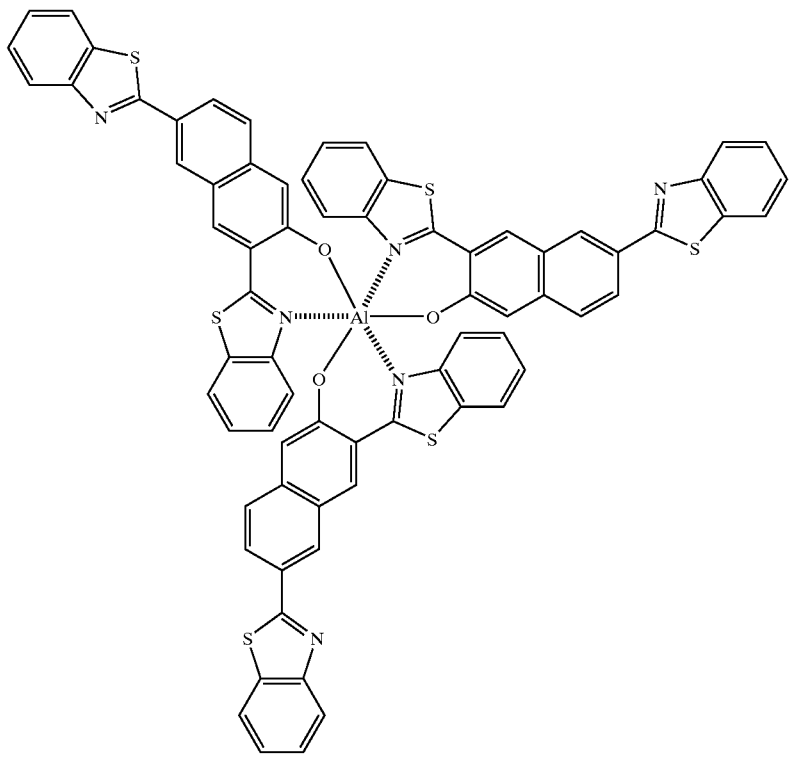

1.23 g of 2-hydroxy-3,6-bis(1',3'-benzothiazol-2'-yl)naphthalene obtained in Example 1-2 was dissolved in 30 g of 1,4-dioxane and 0.13 g of aluminum chloride in 30 g of 1,4-dioxane was added to the solution. The mixture was stirred and heated to 120° C. for 10–20 minutes by means of autoclave, and then, was cooled to room temperature. Precipitates were collected by filtration, washed with 1,4-dioxane and dried to give 0.96 g of yellowish brown crystal of the aluminum complex (decomposition point: 156° C.).

EXAMPLE 6-8

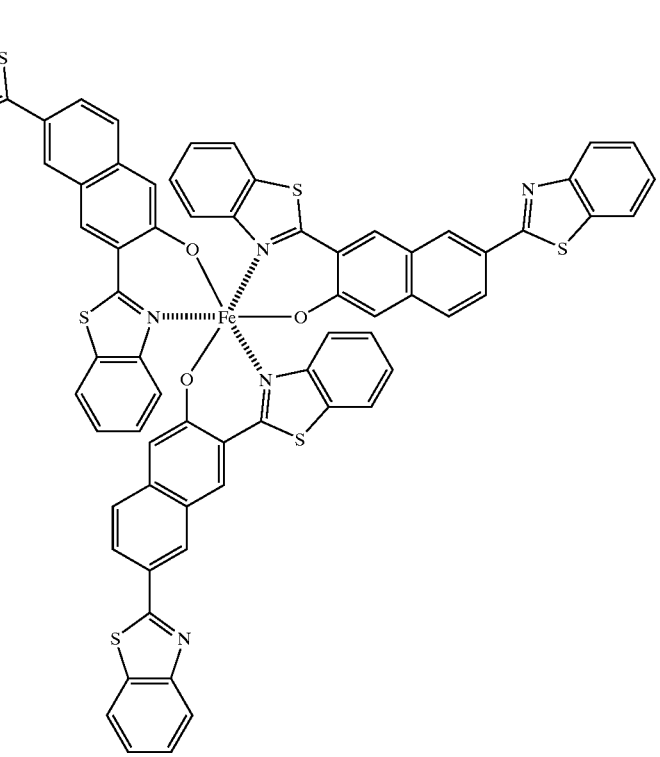

According to the same manner as described in Example 6-7 with the exception that 0.27 g of ferric chloride (III) hexahydrate was used instead of aluminum chloride, 0.99 g of yellowish brown crystal of the ferric (III) complex was obtained (decomposition point 153° C.).

Industrial Applicability

The naphthol derivatives of the present invention can be used as coupler components for azo compounds such as pigments and dyes, as charge generating materials of organic photo conductor as well as structural component of electroluminescent (EL) devices.

The monoazo, bisazo and trisazo compounds of the present invention are preferably used as charge generating materials for organic photo conductors used in electrophotographic copying machines or laser printers.

Further, the monoazo, bisazo and trisazo compounds of the present invention are also useful in the manufacture of pigments, inks, paints, dyes and colorant for polymers.

The metal complexes of the present invention may be used in the manufacture of EL (electroluminescent) device as structural components.

What is claimed is:

1. A naphthol derivative represented by general formula (1):

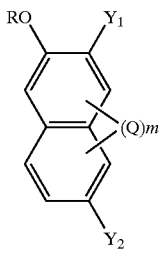

(1)

wherein each $Y_1$ and $Y_2$ is selected from the group consisting of carboxyl, esterified carboxyl, amidated carboxyl groups and a group represented by general formula (2):

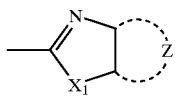

(2)

wherein $X_1$ is —O—, —S— or —NH—,

Z is an optionally substituted aromatic or heterocyclic group having conjugated double bonds, provided that at least one of $Y_1$ and $Y_2$ is the group of formula (2);

Q is selected from the group consisting of optionally branched alkyl and alkoxy groups each having 1–6 carbon atoms, halogen atom, nitro and nitroso groups;

m is an integer of 0–3

R is selected from the group consisting of hydrogen atom, alkaline metal atom, optionally substituted and optionally branched alkyl and acyl groups each having 1–20 carbon atoms, and phenylalkyl group;

or a salt thereof.

2. A monoazo compound represented by general formula (3):

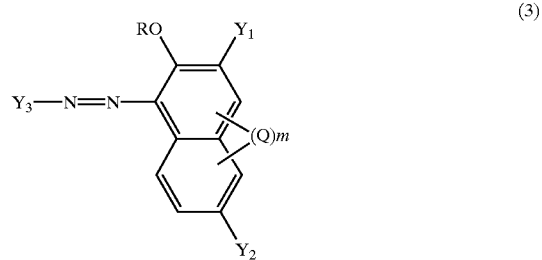

(3)

wherein $Y_1$, $Y_2$, Q, m and R are the same as defined in claim 1, $Y_3$ represents an optionally substituted aromatic group.

3. A bisazo compound represented by general formula (4)

$A_1$—N=N—L—N=N—$A_2$ (4)

wherein $A_1$ and $A_2$ may be the same or different and each is a group of general formula (5)

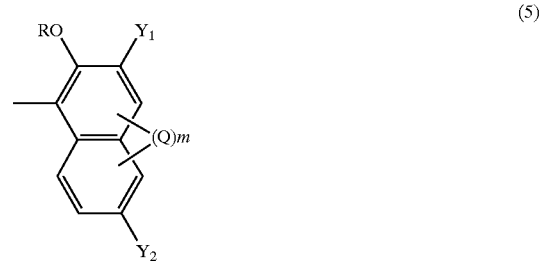

(5)

wherein $Y_1$, $Y_2$, Q, m and R are the same as defined in claim 1;

L is selected from the group consisting of an optionally substituted arylene and groups of general formulae (6) and (7)

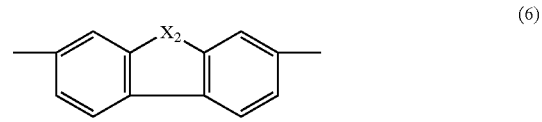

(6)

wherein $X_2$ represents >N—$CH_3$, >C=O or >C=S;

—Ar—M—Ar'— (7)

wherein

Ar and Ar' independently represent an optionally substituted arylene or heterocyclic group having conjugated double bonds;

M is selected from the group consisting of a single bond, —$CH_2$—,13 CH=C($Y_4$)— (wherein $Y_4$ is hydrogen atom, halogen atom, a lower alkyl or cyano group), —O—, —S—, —S—S—, —CO—, —COO—, —$SO_2$—, —N($Y_5$)— (wherein $Y_5$ is an optionally substituted phenyl or alkyl group), —N=N—, —CH=CH—G—CH=CH— (wherein G is arylene group), and a group of general formula (8)

(8)

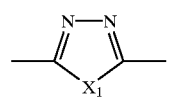

wherein $X_1$ is defined as in claim 1.

4. A trisazo compound represented by general formula (9):

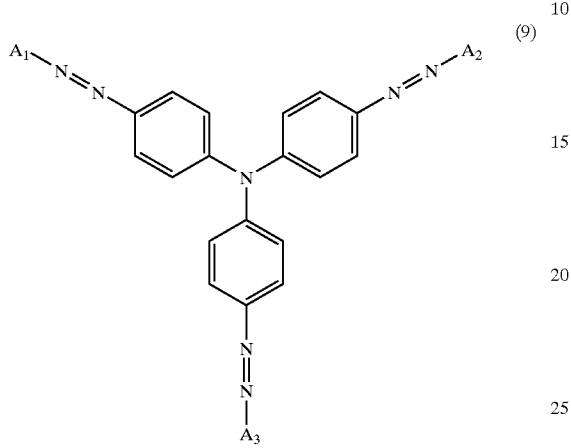

(9)

wherein $A_1$, $A_2$ and $A_3$ may be the same or different and each represents a group of general formula (5)

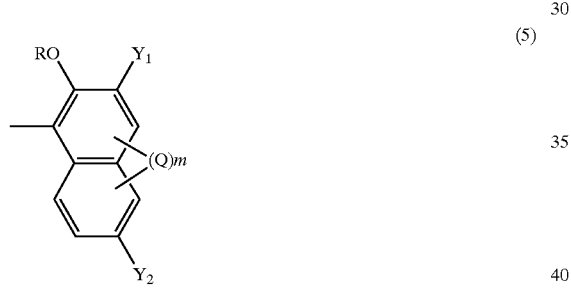

(5)

wherein $Y_1$, $Y_2$, Q, m and R are defined as in claim 1.

5. A method for preparing the trisazo compound of claim 4, which comprises the steps of diazotizing 4,4'4"-triaminophenyl amine represented by formula (10) to give a exazonium salt

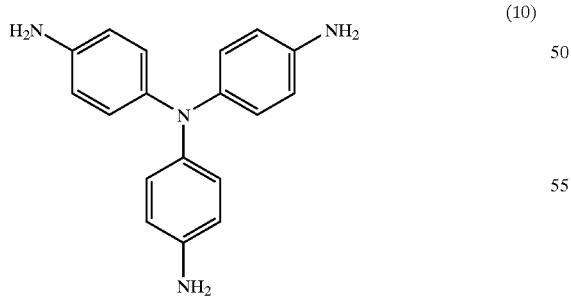

(10)

and coupling the hexazonium salt with the naphthol derivative or a salt thereof of claim 1.

6. A metal complex represented by general formula (11) or (12):

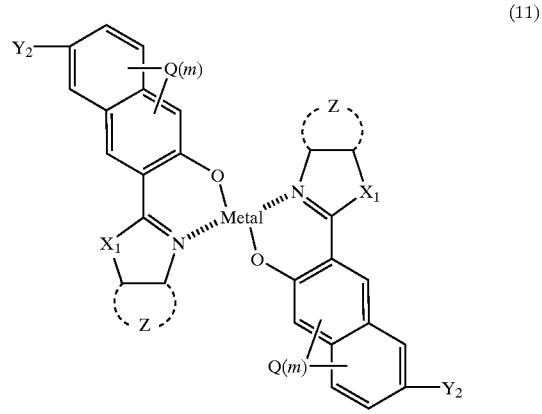

(11)

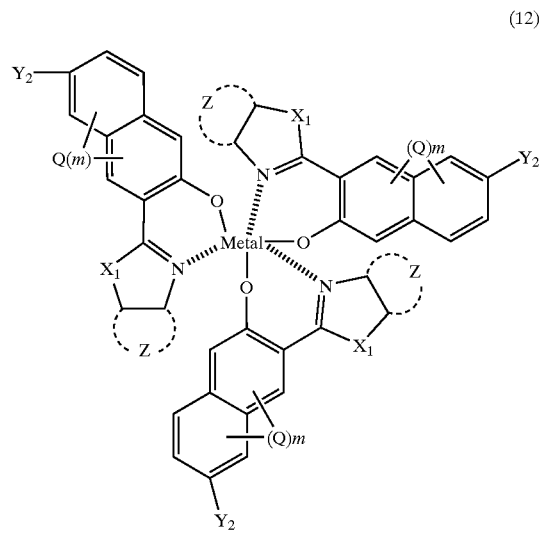

(12)

wherein $Y_2$, $X_1$, Q, m and Z are the same as defined in claim 1, "Metal" represents a metal atom.

7. The metal complex of claim 6, wherein the metal is the one belonging in group 1B, 2B, 3 or 8 of the periodic table.

* * * * *

UNITED STATES PATENT AND TRADEMARK OFFICE
CERTIFICATE OF CORRECTION

PATENT NO. : 6,451,988 B1
DATED : September 17, 2002
INVENTOR(S) : Ryuzo Ueno et al.

It is certified that error appears in the above-identified patent and that said Letters Patent is hereby corrected as shown below:

<u>Title page,</u>
Please add the following information:

-- [30] Foreign Application Priority Data
May 16, 2000 (JP) ………………………….. 2000-143219 --

Signed and Sealed this

Nineteenth Day of August, 2003

JAMES E. ROGAN
*Director of the United States Patent and Trademark Office*